United States Patent
Matthiesen

(10) Patent No.: US 9,388,456 B2
(45) Date of Patent: Jul. 12, 2016

(54) COMPOSITIONS AND METHODS FOR PERFORMING A STRINGENT WASH STEP IN HYBRIDIZATION APPLICATIONS

(75) Inventor: Steen Hauge Matthiesen, Hillerod (DK)

(73) Assignee: DAKO DENMARK A/S, Glostrup (DK)

( * ) Notice: Subject to any disclaimer, the term of this patent is extended or adjusted under 35 U.S.C. 154(b) by 0 days.

(21) Appl. No.: 13/203,149

(22) PCT Filed: Dec. 2, 2009

(86) PCT No.: PCT/IB2009/007917
§ 371 (c)(1),
(2), (4) Date: Aug. 24, 2011

(87) PCT Pub. No.: WO2010/097656
PCT Pub. Date: Sep. 2, 2010

(65) Prior Publication Data
US 2011/0311974 A1   Dec. 22, 2011

Related U.S. Application Data

(60) Provisional application No. 61/155,683, filed on Feb. 26, 2009.

(30) Foreign Application Priority Data

Feb. 27, 2009   (DK) ............................... PA200900278
May 27, 2009   (WO) .................. PCT/IB2009/005893
May 27, 2009   (WO) .................. PCT/IB2009/006548

(51) Int. Cl.
*C12Q 1/68* (2006.01)
*C07H 21/02* (2006.01)
*C07H 21/04* (2006.01)

(52) U.S. Cl.
CPC ............ *C12Q 1/6832* (2013.01); *C12Q 1/6841* (2013.01); *C12Q 2527/125* (2013.01); *C12Q 2527/137* (2013.01)

(58) Field of Classification Search
CPC combination set(s) only.
See application file for complete search history.

(56) References Cited

U.S. PATENT DOCUMENTS

| | | | |
|---|---|---|---|
| 4,888,278 A | 12/1989 | Singer et al. | |
| 4,996,359 A | 2/1991 | Kesling, Jr. et al. | |
| 5,106,730 A * | 4/1992 | Van Ness et al. | 435/6.12 |
| 5,382,285 A | 1/1995 | Morrison | |
| 5,521,061 A | 5/1996 | Bresser et al. | |
| 5,525,492 A * | 6/1996 | Hill | 435/91.2 |
| 5,527,675 A | 6/1996 | Coull et al. | |
| 5,539,082 A | 7/1996 | Nielsen et al. | |
| 5,582,985 A * | 12/1996 | Thompson | 435/6.16 |
| 5,623,049 A | 4/1997 | Lobberding et al. | |
| 5,633,129 A | 5/1997 | Karger et al. | |
| 5,705,333 A | 1/1998 | Shah et al. | |
| 5,714,331 A | 2/1998 | Buchardt et al. | |
| 5,718,915 A | 2/1998 | Virtanen et al. | |
| 5,736,336 A | 4/1998 | Buchardt et al. | |
| 5,750,340 A * | 5/1998 | Kim et al. | 435/6.13 |
| 5,766,855 A | 6/1998 | Buchardt et al. | |
| 5,773,571 A | 6/1998 | Nielsen et al. | |
| 5,786,461 A | 7/1998 | Buchardt et al. | |
| 5,837,459 A | 11/1998 | Berg et al. | |
| 5,869,237 A | 2/1999 | Ward et al. | |
| 5,891,625 A | 4/1999 | Buchardt et al. | |
| 5,925,744 A * | 7/1999 | Haner et al. | 534/15 |
| 5,972,610 A | 10/1999 | Buchardt et al. | |
| 5,986,053 A | 11/1999 | Ecker et al. | |
| 6,107,470 A | 8/2000 | Nielsen et al. | |
| 6,201,103 B1 | 3/2001 | Nielsen et al. | |
| 6,228,982 B1 | 5/2001 | Norden et al. | |
| 6,331,618 B1 * | 12/2001 | Bloch et al. | 536/25.4 |
| 6,357,163 B1 | 3/2002 | Buchardt et al. | |
| 6,475,720 B1 | 11/2002 | Gray et al. | |
| 6,555,670 B1 * | 4/2003 | Aizawa et al. | 536/23.5 |
| 6,656,685 B2 | 12/2003 | Utermohlen et al. | |
| 6,670,461 B1 | 12/2003 | Wengel et al. | |
| 6,794,499 B2 | 9/2004 | Wengel et al. | |
| 7,034,133 B2 | 4/2006 | Wengel et al. | |
| 7,374,945 B2 | 5/2008 | Becker | |
| 7,572,582 B2 | 8/2009 | Wengel et al. | |
| 7,750,208 B2 | 7/2010 | Huang et al. | |
| 7,867,443 B2 | 1/2011 | Key et al. | |
| 8,034,909 B2 | 10/2011 | Wengel et al. | |
| 8,080,644 B2 | 12/2011 | Wengel et al. | |
| 8,153,365 B2 | 4/2012 | Wengel et al. | |
| 2001/0000487 A1 | 4/2001 | Essenfeld et al. | |
| 2001/0007748 A1 | 7/2001 | An et al. | |
| 2001/0009766 A1 | 7/2001 | Bard et al. | |
| 2001/0010936 A1 | 8/2001 | Richards et al. | |
| 2001/0011131 A1 | 8/2001 | Luyten et al. | |
| 2001/0018512 A1 | 8/2001 | Blanchard | |
| 2001/0026919 A1 | 10/2001 | Chenchik et al. | |
| 2001/0027567 A1 | 10/2001 | Federoff | |
| 2001/0056203 A1 | 12/2001 | Sezi et al. | |

(Continued)

FOREIGN PATENT DOCUMENTS

EP   1 013 772 A1   6/2000
EP   1013772   6/2000

(Continued)

OTHER PUBLICATIONS

LyondellBasell (retrieved on Mar. 7, 2013 from the internet < http://www.lyondellbasell.com/techlit/techlit/2313.pdf>).*
Bioprotocols (retrieved on Jul. 28, 2014 from the internet: http://www.bioprotocols.info/reagent_and_buffer_recipes/20x-SSC.php).*
Kurreck, "Improvement through novel chemical modifications" Eur. J. Biochem. 270:1628-1644 (2003).

(Continued)

*Primary Examiner* — Robert T Crow
*Assistant Examiner* — Joseph G Dauner

(57) ABSTRACT

The invention provides methods and compositions for performing a stringent wash step in a hybridization assay between at least one molecule and a target. The invention may, for example, eliminate the use of, or reduce the dependence on formamide in the stringent wash step. Compositions for use in the invention include an aqueous composition comprising at least one polar aprotic solvent in an amount effective to denature non-complementary sequences in a hybridization product.

15 Claims, 2 Drawing Sheets

(56) References Cited

U.S. PATENT DOCUMENTS

| | | |
|---|---|---|
| 2002/0150904 A1 | 10/2002 | Bi et al. |
| 2002/0164614 A1 | 11/2002 | Becker |
| 2002/0182613 A1 | 12/2002 | Mirkin et al. |
| 2002/0197629 A1 | 12/2002 | Gjerde |
| 2002/0198366 A1 | 12/2002 | Ashkenazi et al. |
| 2003/0108903 A1 | 6/2003 | Wang et al. |
| 2003/0175852 A1 | 9/2003 | Kalra et al. |
| 2004/0029184 A1 | 2/2004 | Gourevitch |
| 2004/0030093 A1 | 2/2004 | Sakurai et al. |
| 2004/0048376 A1 | 3/2004 | Chabot et al. |
| 2004/0053222 A1 | 3/2004 | Storhoff et al. |
| 2004/0096967 A1 | 5/2004 | Gryseels et al. |
| 2004/0122101 A1* | 6/2004 | Miller et al. ............. 514/575 |
| 2004/0210967 A1 | 10/2004 | Chen et al. |
| 2004/0241666 A1* | 12/2004 | Amorese et al. ............. 435/6 |
| 2005/0014154 A1* | 1/2005 | Weizenegger ............. 435/6 |
| 2005/0191657 A1 | 9/2005 | Demorest et al. |
| 2005/0234236 A1* | 10/2005 | Kertesz et al. ............. 544/239 |
| 2005/0266459 A1 | 12/2005 | Poulsen et al. |
| 2006/0030541 A1 | 2/2006 | Garcia et al. |
| 2006/0147957 A1 | 7/2006 | Qian et al. |
| 2006/0148846 A1* | 7/2006 | Orwat et al. ............. 514/303 |
| 2007/0148657 A1 | 6/2007 | Myerson et al. |
| 2007/0243545 A1 | 10/2007 | Kilpatrick et al. |
| 2008/0044385 A1 | 2/2008 | Nishi et al. |
| 2008/0227653 A1 | 9/2008 | Fodor et al. |
| 2009/0123913 A1 | 5/2009 | Barany et al. |
| 2009/0197346 A1 | 8/2009 | Winkler et al. |
| 2009/0221429 A1 | 9/2009 | Fujimoto et al. |
| 2009/0294305 A1 | 12/2009 | Bekki et al. |
| 2011/0250698 A1 | 10/2011 | Pollner et al. |
| 2011/0262930 A1 | 10/2011 | Deleersnijder et al. |
| 2011/0281263 A1 | 11/2011 | Matthiesen et al. |
| 2012/0331587 A1 | 12/2012 | Lassen et al. |
| 2013/0017176 A1 | 1/2013 | Hosoda et al. |
| 2013/0156695 A1 | 6/2013 | Sprecher et al. |
| 2013/0230918 A1 | 9/2013 | Wakamiya |

FOREIGN PATENT DOCUMENTS

| | | |
|---|---|---|
| WO | WO 91/02088 A1 | 2/1991 |
| WO | WO 92/07956 A1 | 5/1992 |
| WO | WO 94/02638 A1 | 2/1994 |
| WO | WO 94/02639 | 2/1994 |
| WO | WO 96/04000 | 2/1996 |
| WO | WO 99/14226 | 3/1999 |
| WO | WO 00/69899 | 11/2000 |
| WO | WO 00/69899 A1 | 11/2000 |
| WO | WO 01/66804 A2 | 9/2001 |
| WO | WO 02/061137 | 8/2002 |
| WO | WO 03/014398 A2 | 2/2003 |
| WO | WO 03/027328 | 4/2003 |
| WO | WO 03/054209 | 7/2003 |
| WO | WO 2006/007841 | 1/2006 |
| WO | WO 2006/066039 | 6/2006 |
| WO | WO 2006/117596 | 11/2006 |
| WO | WO 2007/058326 | 11/2006 |
| WO | WO 2007/019492 A2 | 2/2007 |
| WO | WO 2007/037341 A1 | 4/2007 |
| WO | WO 2007/109941 | 9/2007 |
| WO | WO 2009/074154 | 6/2009 |
| WO | WO 2009/144581 | 12/2009 |
| WO | WO 2009/147537 | 12/2009 |

OTHER PUBLICATIONS

Powell, et al., "Metallographic in situ hybridization" Human Pathology, 38:1145-1159 (2007).
Boehringer Mannheim "Nucleic Acid Hybridization—General Aspects" Biochemicals Catalog, Jan. 1, 1992, pp. 14-17.
International Search Report and Written Opinion issued in International Patent Application No. PCT/IB2009/007917 (WO 2010/097656); Date of Mailing: Apr. 28, 2010 (10 pages).
2-pyrrolidone, Wikapedia Webpage, Nov. 1, 2012 (1 page).
Beebe, "Glycerin Antigen Retrieval," Microscopy Today, 9:30-31, 1999 (3 pages).
Brown et al., Analysis of RNA by Northern and Slot Blot Hybridization, Current Protocols in Molecular Biology, Unit 4.9 (19 pages).
Chakrabarti et al., "The enhancement of PCR amplification by low-molecular weight sulfones," *Gene*, 274:293-298, 2001 (6 pages).
Chakrabarti et al., "The enhancement of PCR amplification by low molecular weight sulfones," *Nucleic Acids research*, 29(11):2377-2387, 2001 (5 pages).
Chardonnet et al., "Human papillomavirus detection in cervical cells by in situ hybridization with biotinylated probes," *Cytopathy*, 3(6):341-350, 1992 (10 pages).
Dako catalog, "TOP2A Fish pharmDxTM Kit," pp. 1-33, May 24, 2007 (34 pages).
DOW Ethylene Glycols, Webpage, Jun. 28, 2012 (2 pages).
DOW Propylene Glycol, Webpage, Jun. 28, 2012 (2 pages).
Extended European Search Report from the European Patent Office for corresponding EP Application No. 13164099.7, Aug. 14, 2013 (5 pages).
Extended European Search Report from the European Patent Office for corresponding EP Application No. 13164094.8, Aug. 8, 2013 (5 pages).
Hayat, editor, "Factors Affecting Antigen Retrieval," Chapter 4 of Microscopy, Immunohistochemistry and Antigen Retrieval, New York, p. 71-93, 2002 (23 pages).
International Search Report issued Jun. 16, 2008 for International Application No. PCT/DK2008/000066 (3 pages).
International Search Report and Written Opinion issued Sep. 22, 2009 for International Application No. PCT/IB2009/005893 (14 pages).
International Search Report and Written Opinion issued Feb. 15, 2010 for International Application No. PCT/IB2009/006548 (14 pages).
International Search Report and Written Opinion issued May 7, 2010 for International Application No. PCT/IB2009/007725 (18 pages).
International Search Report and Written Opinion issued Jul. 12, 2010 for International Application No. PCT/IB2010/00659 (16 pages).
Luo et al., "Establishment of a simple and useful way for preimplantation genetic diagnosis of chromosomal diseases," *J. Huazhong Univ. Science & Tech.*, 27(3):315-317, 2007 (3 pages).
Markarian et al., "Effect of Diethylsulfoxide on the Thermal Denaturation of DNA," Department of Chemistry, Yerevan State University, Armenia, Jan. 19, 2006 (5 pages).
Mochizuki et al., "Solvent effect on PCR from a viewpoint of a change of microscopic environment of Mg(2+) in a solution," *Biochem. Biophys. Res. Commun.*, Jun. 6, 2007 (Abstract Only) (1 page).
Moroni et al., "Gene copy number for epidermal growth factor receptor (EGFR) and clinical response to antiEGFR treatment in colorectal cancer: a cohort study," *Lancet Oncol.*, 6:279-286, 2005 (8 pages).
Notice of Allowance, Examiner-Initiated Interview Summary, and Reasons for Allowability, issued Feb. 20, 2013, in U.S. Appl. No. 12/526,323, filed Feb. 16, 2010. (10 pages).
Nielsen et al., "PNA suppression method combined with fluorescence in situ hybridization (FISH) technique," Chapter 10 of PRINS and PNA Technologies in Chromosomal Investigation (Ed. Franck Pellestor), 2006 (22 pages).
Office Action, issued Jul. 17, 2012, in U.S. Appl. No. 12/526,323, filed Feb. 16, 2010 (16 pages).
Office Action issued Nov. 6, 2012, in U.S. Appl. No. 12/994,495, filed May 23, 2011 (20 pages).
Office Action issued May 6, 2013, in U.S. Appl. No. 12/994,495, filed May 23, 2011 (17 pages).
Office Action, issued Sep. 24, 2013, in U.S. Appl. No. 13/203,160 (31 pages).
Office Action, issued Sep. 18, 2013, in U.S. Appl. No. 13/203,137 (33 pages).
Office Action, issued Feb. 20, 2013, in U.S. Appl. No. 12/526,323 (10 pages).
Olsen et al., "Amplification of HER2 and TOP2A and deletion of TOP2A genes in breast cancer investigated by new FISH probes," *Acta Oncologia* 43(1):35, 2004 (8 pages).

(56) References Cited

OTHER PUBLICATIONS

Optim synthetic Glycerine—Vapor Pressure and Boiling Point, Webpage, Jun. 28, 2012 (1 page).

Shapiro et al., "Detection of N-myc gene amplification by fluorescence in situ hybridization," *Am. J. Pathology*, 145(5): 1339, 1993 (8 pages).

Stratagene Catalogue, p. 39, 1988 (2 pages).

Superscript™ First-Strand Synthesis System for RT-PCR, Invitrogen document dated Mar. 5, 2007 (4 pages).

Tkachuk et al., "Detection of bcr-abl fusion in Chronic Myelogenous Leukemia by in situ hybridization," *Science* 250:559, 1990 (4 pages).

Wahl, G. et al., "Efficient transfer of large DNA fragments from agarose gels to diazobenzyloxymethyl-paper and rapid hybridization by using dextran sulfate," *Proc. Natl. Acad. Sci.*, Aug. 1979, pp. 3683-3687, vol. 7, No. 8 (5 pages).

Woenckhause et al., "Multitarget FISH and LOH analysis at chromosome 3p in non-small cell lung cancer and adjacent bronchial epithelium," *Am. J. of Clin. Pathol.*, 123:752, 2005 (10 pages).

Kiyama, Hiroshi et al., "*In Situ Hybridization Method*," New Genetic Engineering Handbook, Experimental Medical Edition, Muramatsu Masami, et al. Editors, pp. 202-203, Apr. 20, 1996.

Toyozo, Takahashi, "*Principal Assay Method in Infection Diagnosis, Chapter 3 Diagnosis of Infection by DNA Probe*," Applied DNA Probe Technology, pp. 36-39, Feb. 5, 1998.

Ahern, Holly, "*Biochemical, reagents kits offer scientists good return on investment*," The Scientist, 9(15):20 (Jul. 24, 1995).

Cox, W., et al., "*Fluorescent DNA hybridization probe preparation using amine modification and reactive dye coupling*," Biotechniques 36:114-122 (Jan. 2004).

Huber C. and Berti G., "*Detection of Partial Denaturation in AT-Rich DNA Fragments By Ion-Pair Reserved-Phase Chromatography*," Anal. Chem., 68(17):2959 (Sep. 1, 1996).

Rigby S. et al., "*Fluorescence in Situ Hybridization with Peptide Nucleic Acid Probes For Rapid Identifications of Candida Albicans Directly from Blood Culture Bottles*," Journal of Clinical Microbiology, 4(6): 2182 (Jun. 2002).

Summersgill B. et al., "*Fluorescence and Chromogenic in situ hybridization to detect genetic aberrations in formalin-fixed paraffin embedded material, including tissue microarrays*," Natural Protocols, 3(2): 220 (Feb. 2008).

Xi C. et al., "*Use of DNA and Peptide Nucleic Acid Molecular Beacons for Detection and Quantification of rRNA in Solution and in Whole Cells*," Applied and Environmental Microbiology, 69(9): 5673 (Sep. 2003).

Office Action for U.S. Appl. No. 13/203,160 dated Jun. 25, 2014 (24 pages).

Office Action for U.S. Appl. No. 12/994,492 dated May 7, 2014 (7 pages).

Office Action for U.S. Appl. No. 13/203,137 dated Jun. 10, 2014 (20 pages).

Office Action for U.S. Appl. No. 13/513,164 dated Aug. 22, 2014 (51 pages).

Office Action for U.S. Appl. No. 12/994,495 dated Aug. 12, 2014 (20 pages).

\* cited by examiner

COMPOSITIONS AND METHODS FOR PERFORMING A STRINGENT WASH STEP IN HYBRIDIZATION APPLICATIONS

CROSS-REFERENCE TO RELATED APPLICATIONS

This application is a National Stage Entry of International Application No. PCT/IB2009/007917, filed on Dec. 2, 2009, which claims priority from U.S. Provisional Application 61/155,683, filed on Feb. 26, 2009.

FIELD OF THE INVENTION

The present invention relates to compositions and methods for performing a stringent wash step in hybridization applications In one embodiment, the present invention can be used for the in vivo, in vitro, and in situ molecular examination of DNA and RNA. In particular, the invention can be used for the molecular examination of DNA and RNA in the fields of cytology, histology, and molecular biology. In other embodiments, the present invention can be used for in situ hybridization (ISH) applications.

BACKGROUND AND DESCRIPTION

Double stranded nucleic acid molecules (i.e., DNA (deoxyribonucleic acid), DNA/RNA (ribonucleic acid) and RNA/RNA) associate in a double helical configuration. This double helix structure is stabilized by hydrogen bonding between bases on opposite strands when bases are paired in a particular way (A+T/U or G+C) and hydrophobic bonding among the stacked bases. Complementary base paring (hybridization) is central to all processes involving nucleic acid.

In a basic example of hybridization, nucleic acid probes or primers are designed to bind, or "hybridize," with a target nucleic acid, for example, DNA or RNA in a sample. One type of hybridization application, in situ hybridization (ISH), includes hybridization to a target in a specimen wherein the specimen may be in vivo, in situ, or for example, fixed or adhered to a glass slide.

The efficiency and accuracy of nucleic acid hybridization assays mostly depend on at least one of three major factors: a) denaturation (i.e., separation of, e.g., two nucleic acid strands) conditions, b) renaturation (i.e., re-annealing of, e.g., two nucleic acid strands) conditions, and c) post-hybridization washing conditions.

Traditional hybridization experiments, such as ISH assays, use a formamide-containing solution to denature doubled stranded nucleic acid. Formamide disrupts base pairing by displacing loosely and uniformly bound hydrate molecules and by causing "formamidation" of the Watson-Crick binding sites. Thus, formamide has a destabilizing effect on double stranded nucleic acids and analogs.

Once the complementary strands of nucleic acid have been separated, a "renaturation" or "reannealing" step allows the primers or probes to bind to the target nucleic acid in the sample. This step is also sometimes referred to as the "hybridization" step. The re-annealing step is by far the most time-consuming aspect of traditional hybridization applications. See FIGS. 1 and 2 (presenting examples of traditional hybridization times). In addition, the presence of formamide in a hybridization buffer can significantly prolong the renaturation time, as compared to aqueous denaturation solutions without formamide.

After the complementary strands of nucleic acid have reannealed, any unbound and mis-paired probe is removed by a series of post-hybridization washes. The specificity of the interaction between the probe and the target is largely determined by stringency of these post-hybridization washes. Duplexes containing highly complementary sequences are more resistant to high-stringency conditions than duplexes with low complementary. Thus, increased stringency conditions can be used to remove non-specific bonds between the probe and the target nucleic acids.

Four main variables are typically adjusted to influence the stringency of the post-hybridization washes:
1. Temperature (as temperature increases, non-perfect matches between the probe and the target sequence will denature, i.e., separate, before more perfectly matched sequences).
2. Salt conditions (as salt concentration decreases, non-perfect matches between the probe and the target sequence will denature, i.e., separate, before more perfectly matched sequences).
3. Formamide concentration (as the amount of formamide increases, non-perfect matches between the probe and the target sequence will denature, i.e., separate, before more perfectly matched sequences).
4. Time (as the wash time increases, non-perfect matches between the probe and the target sequence will denature, i.e., separate, before more perfectly matched sequences).

Other factors such as pH, rate of agitation, and number of washes will also influence the stringency of the wash step. However, the use of high temperatures and/or high formamide concentrations can have significant drawbacks. For example, heat can be destructive to membranes, sample morphology, and to the nucleic acid itself. Heat can lead to complications when small volumes are used, since evaporation of aqueous buffers is difficult to control. In addition, formamide is a toxic, hazardous material, subject to strict regulations for use and waste. Furthermore, the use of a high concentration of formamide appears to cause morphological destruction of cellular, nuclear, and/or chromosomal structure.

Thus, a need exists for overcoming the drawbacks associated with the traditional post-hybridization washes of hybridization applications. By addressing this need, the present invention provides several potential advantages over prior art hybridization applications, such as increased specificity, lower background, lower wash temperatures, preservation of sample morphology, and less toxic hybridization solvents.

SUMMARY OF THE INVENTION

It is an object of the present invention to provide compositions which result in at least one of the following advantages: increased specificity, lower background, lower evaporation of reagent, preservation of sample morphology, simpler procedure, faster procedure, easier automation, and safer reagents. One way in which the present invention achieves those objectives is by providing compositions and methods for performing a stringent wash step in hybridization applications.

The compositions and methods of the invention are applicable to any hybridization technique. The compositions and methods of the invention are also applicable to any molecular system that hybridizes or binds using base pairing, such as, for example, DNA, RNA, PNA, LNA, and synthetic and natural analogs thereof.

The method and compositions of the present invention may be used for the in vivo, in vitro, or in situ analysis of genomic DNA, chromosomes, chromosome fragments, genes, and chromosome aberrations such as translocations, deletions, amplifications, insertions, mutations, or inversions associated with a normal condition or a disease. Further, the methods and compositions are useful for detection of infectious agents as well as changes in levels of expression of RNA, e.g., mRNA and its complementary DNA (cDNA).

Other uses include the in vivo, in vitro, or in situ analysis of messenger RNA (mRNA), viral RNA, viral DNA, small interfering RNA (siRNA), small nuclear RNA (snRNA), noncoding RNA (ncRNA, e.g., tRNA and rRNA), transfer messenger RNA (tmRNA), micro RNA (miRNA), piwi-interacting RNA (piRNA), long noncoding RNA, small nucleolar RNA (snoRNA), antisense RNA, double-stranded RNA (dsRNA), methylations and other base modifications, single nucleotide polymorphisms (SNPs), copy number variations (CNVs), and nucleic acids labeled with, e.g., radioisotopes, fluorescent molecules, biotin, digoxigenin (DIG), or antigens, alone or in combination with unlabeled nucleic acids.

The method and compositions of the present invention are useful for in vivo, in vitro, or in situ analysis of nucleic acids using techniques such as northern blot, Southern blot, flow cytometry, autoradiography, fluorescence microscopy, chemiluminescence, immunohistochemistry, virtual karyotype, gene assay, DNA microarray (e.g., array comparative genomic hybridization (array CGH)), gene expression profiling, Gene ID, Tiling array, gel electrophoresis, capillary electrophoresis, and in situ hybridizations such as FISH, SISH, CISH. The methods and compositions of the invention may be used on in vitro and in vivo samples such as bone marrow smears, blood smears, paraffin embedded tissue preparations, enzymatically dissociated tissue samples, bone marrow, amniocytes, cytospin preparations, imprints, etc.

In one embodiment, the invention provides methods and compositions for performing a stringent wash step in hybridization applications. The invention may, for example, eliminate the use of, or reduce the dependence on formamide from, e.g., 50% formamide in traditional stringent wash buffers to 25%, 15%, 10%, 5%, 2%, 1% or 0% formamide in the compositions and methods of the invention.

The methods and compositions of the invention may also increase the stringency of post-hybridization washes without the use of formamide such that the stringent wash can occur, e.g., at a lower temperature than with traditional non-formamide stringent wash buffers.

The invention may also allow for stringency washes at lower temperatures (e.g. 20-30° C. lower) than traditional hybridization applications. For example, instead of washing single locus probes at 73° C. in 1×SSC, 0.3% NP-40, the compositions and methods of the invention may allow such probes to be washed at 45° C., or 40° C., or 35° C., or even at room temperature. The invention may also allow the stringent wash to be performed at the same or at a lower temperature than the hybridization temperature.

Thus, in some aspects, the present invention overcomes major toxicity and temperature problems associated with traditional hybridization assays by allowing for easier automation, by lowering the stringent wash temperature of, e.g., single locus probes without using the toxic chemical formamide, and by providing stringent wash temperatures that cause less harm to, e.g., biological samples (such as, virus, RNA, DNA, FFPE tissue sections, cryo sections, cytological preparations, etc.) and/or their potential carriers (e.g. nitrocellulose membranes, microarrays, etc).

One aspect of the invention is a composition or solution for use in post-hybridization stringency washes. Compositions for use in the invention include an aqueous composition comprising at least one polar aprotic solvent in an amount effective to denature non-complementary double-stranded nucleotide sequences. One way to test for whether the amount of polar aprotic solvent is effective to denature non-complementary sequences in a hybridization product is to determine whether the polar aprotic solvent, when used in the methods and compositions described herein, yields a signal to noise ratio of 2× (or higher) than that observed for an unrelated probe in the particular hybridization assay.

Non-limiting examples of effective amounts of polar aprotic solvents include, e.g., about 1% to about 95% (v/v). In some embodiments, the concentration of polar aprotic solvent is 5% to 60% (v/v). In other embodiments, the concentration of polar aprotic solvent is 10% to 60% (v/v). In still other embodiments, the concentration of polar aprotic solvent is 30% to 50% (v/v). Concentrations of 1% to 5%, 5% to 10%, 10%, 10% to 20%, 20% to 30%, 30% to 40%, 40% to 50%, 50% to 60%, or 60% to 70% (v/v) are also suitable. In some embodiments, the polar aprotic solvent will be present at a concentration of 0.1%, 0.25%, 0.5%, 1%, 2%, 3%, 4%, or 5% (v/v). In other embodiments, the polar aprotic solvent will be present at a concentration of 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v).

According to another aspect of the present invention the aqueous composition comprising a polar aprotic solvent has reduced toxicity compared to traditional formamide-containing stringency wash solutions. For example, a less-toxic composition of the invention may comprise a composition with the proviso that the composition does not contain formamide, or with the proviso that the composition contains less than 25%, or less than 10%, or less than 5%, or less than 2%, or less than 1%, or less than 0.5%, or less than 0.1%, or less than 0.05%, or less than 0.01% formamide. A less-toxic composition may also comprise a composition with the proviso that the composition does not contain dimethyl sulfoxide (DMSO), or with the proviso that the composition contains less than 25%, 10%, 5%, 2%, or less than 1%, or less than 0.5%, or less than 0.1%, or less than 0.05%, or less than 0.01% DMSO.

In one aspect of the invention, suitable polar aprotic solvents for use in the invention may be selected based on their Hansen Solubility Parameters. For example, suitable polar aprotic solvents may have a dispersion solubility parameter between 17.7 to 22.0 MPa$^{1/2}$, a polar solubility parameter between 13 to 23 MPa$^{1/2}$, and a hydrogen bonding solubility parameter between 3 to 13 MPa$^{1/2}$.

According to one aspect of the present invention, suitable polar aprotic solvents for use in the invention are cyclic compounds. A cyclic compound has a cyclic base structure.

Examples include the cyclic compounds disclosed herein. In other embodiments, the polar aprotic solvent may be chosen from Formulas 1-4 below:

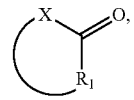

Formula 1

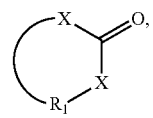

Formula 2

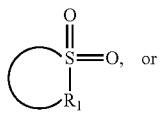

Formula 3

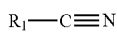

Formula 4 where X is O and R1 is alkyldiyl.

According to another aspect of the invention, suitable polar aprotic solvents for use in the invention may be chosen from Formula 5 below:

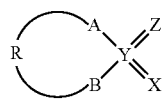

Formula 5 where X is optional and if present, is chosen from O or S;
where Z is optional and if present, is chosen from O or S;
where A and B independently are O or N or S or part of the alkyldiyl or a primary amine;
where R is alkyldiyl; and
where Y is O or S or C.

Examples of suitable polar aprotic solvents according to Formula 5 are provided in Formulas 6-9 below:

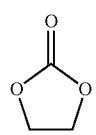

Formula 6 where:
X is non-existing;
A, B, and Z are O;
Y is C; and
R is Ethane-1,2 diyl;

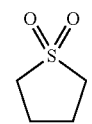

Formula 7 where:
Z and X are O;
A and B are part of the alkyldiyl;
Y is S; and
R is Butane-1,4 diyl;

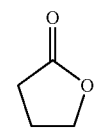

Formula 8 where:
X is non-existing;
A is part of the alkyldiyl;
Y is C;
B and Z is O; and
R is Propane-1,3 diyl;

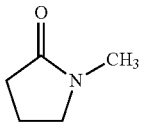

Formula 9 where:
X is non-existing;
A is part of the alkyldiyl;
Y is C;
B is methylamine;
Z is O; and
R is Propane-1,3 diyl According to yet another aspect of the invention the polar aprotic solvent has lactone, sulfone, nitrile, sulfite, or carbonate functionality. Such compounds are distinguished by their relatively high dielectric constants, high dipole moments, and solubility in water.

According to another aspect of the invention the polar aprotic solvent having lactone functionality is γ-butyrolactone (GBL), the polar aprotic solvent having sulfone functionality is sulfolane (SL), the polar aprotic solvent having nitrile functionality is acetonitrile (AN), the polar aprotic solvent having sulfite functionality is glycol sulfite/ethylene sulfite (GS), and the polar aprotic solvent having carbonate functionality is ethylene carbonate (EC), propylene carbonate (PC), or ethylene thiocarbonate (ETC). In yet another aspect of the invention, the compositions and methods of the invention comprise a polar aprotic solvent, with the proviso that the polar aprotic solvent is not acetonitrile (AN) or sulfolane (SL).

According to yet another aspect, the invention discloses a method for performing a stringent wash step in a hybridization application comprising:
a) providing a hybridization product comprising a first nucleic acid sequence hybridized to a second nucleic acid sequence,
b) providing an aqueous composition comprising at least one polar aprotic solvent in an amount effective to denature non-complementary double-stranded nucleotide sequences, and
c) combining the hybridization product and the aqueous composition for at least a time period sufficient to denature any non-complementary binding between the first and second nucleic acid sequences.

In one embodiment, no additional energy is required to denature any non-complementary binding between the first and second nucleic acid sequences. In other embodiments, a sufficient amount of energy to denature any non-complementary binding between the first and second nucleic acid sequences is provided.

According to yet another aspect of the present invention, the energy is provided by heating the aqueous composition and the hybridization product. Thus, the step of method of the invention may include the steps of heating and cooling the aqueous composition and nucleic acid sequences.

A further aspect of the invention, the energy is provided by the use of microwaves, hot baths, hot plates, heat wire, peltier element, induction heating, or heat lamps.

In one embodiment, the aqueous composition and hybridization product are heated to less than 70° C., such as, for example, 65° C., 62° C., 60° C., 55° C., 52° C., 50° C., 45° C., 42° C., or 40° C.

In one embodiment, the denaturation of any non-complementary binding between the first and second nucleic acid sequences occurs in less than 1 hour, such as, for example, 45 minutes, 30 minutes, 15 minutes, 10 minutes, 5 minutes, or 1 minute.

According to a further aspect, the invention relates to the use of a composition comprising between 1 and 95% (v/v) of at least one polar aprotic solvent in a stringent wash step in a hybridization application.

According to yet another aspect, the invention relates to the use of a an aqueous composition as described in this invention for performing a stringent wash step in a hybridization application.

DETAILED DESCRIPTION

A. Definitions

Figure 1:
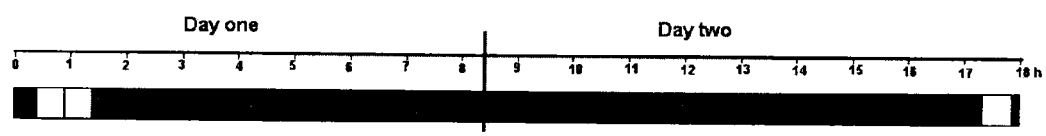
FIG. 1 depicts a typical time-course for single locus hybridization assay with primary labeled FISH probes on formaldehyde fixed paraffin embedded tissue sections (histological specimens). The first bar on the left represents the deparaffination step; the second bar represents the heat-pretreatment step; the third bar represents the digestion step; the fourth bar represents the denaturation and hybridization steps; the fifth bar represents the stringency wash step; and the sixth bar represents the mounting step.
Figure 2:
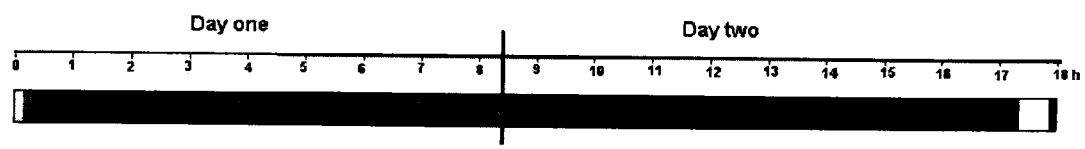
FIG. 2 depicts a typical time-course for single locus hybridization assay with primary labeled FISH probes on cytological specimens. The first bar on the left represents the fixation step; the second bar represents the denaturation and hybridization steps; the third bar represents the stringency wash step; and the fourth bar represents the mounting step.

In the context of the present invention the following terms are to be understood as follows:

"Biological sample" is to be understood as any in vivo, in vitro, or in situ sample of one or more cells or cell fragments. This can, for example, be a unicellular or multicellular organism, tissue section, cytological sample, chromosome spread, purified nucleic acid sequences, artificially made nucleic acid sequences made by, e.g., a biologic based system or by chemical synthesis, microarray, or other form of nucleic acid chip. In one embodiment, a sample is a mammalian sample, such as, e.g., a human, murine, rat, feline, or canine sample.

"Nucleic acid," "nucleic acid chain," and "nucleic acid sequence" mean anything that binds or hybridizes using base pairing including, oligomers or polymers having a backbone formed from naturally occurring nucleotides and/or nucleic acid analogs comprising nonstandard nucleobases and/or nonstandard backbones (e.g., a peptide nucleic acid (PNA) or locked nucleic acid (LNA)), or any derivatized form of a nucleic acid.

As used herein, the term "peptide nucleic acid" or "PNA" means a synthetic polymer having a polyamide backbone with pendant nucleobases (naturally occurring and modified), including, but not limited to, any of the oligomer or polymer segments referred to or claimed as peptide nucleic acids in, e.g., U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 6,201,103, 6,228,982 and 6,357,163, WO96/04000, all of which are herein incorporated by reference, or any of the references cited therein. The pendant nucleobase, such as, e.g., a purine or pyrimidine base on PNA may be connected to the backbone via a linker such as, e.g., one of the linkers taught in PCT/US02/30573 or any of the references cited therein. In one embodiment, the PNA has an N-(2-aminoethyl)-glycine) backbone. PNAs may be synthesized (and optionally labeled) as taught in PCT/US02/30573 or any of the references cited therein. PNAs hybridize tightly, and with high sequence specificity, with DNA and RNA, because the PNA backbone is uncharged. Thus, short PNA probes may exhibit comparable specificity to longer DNA or RNA probes. PNA probes may also show greater specificity in binding to complementary DNA or RNA.

As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, Eur. J. Biochem., 270:1628-44 (2003).

Examples of nucleic acids and nucleic acid analogs also include polymers of nucleotide monomers, including double and single stranded deoxyribonucleotides (DNA), ribonucleotides (RNA), α-anomeric forms thereof, synthetic and natural analogs thereof, and the like. The nucleic acid chain may be composed entirely of deoxyribonucleotides, ribonucleotides, peptide nucleic acids (PNA), locked nucleic acids (LNA), synthetic or natural analogs thereof, or mixtures thereof. DNA, RNA, or other nucleic acids as defined herein can be used in the method and compositions of the invention.

"Polar aprotic solvent" refers to an organic solvent having a dipole moment of about 2 debye units or more, a water solubility of at least about 5% (volume) at or near ambient temperature, i.e., about 20° C., and which does not undergo significant hydrogen exchange at approximately neutral pH, i.e., in the range of 5 to 9, or in the range 6 to 8. Polar aprotic solvents include those defined according to the Hansen Solubility Parameters discussed below.

"Alkyldiyl" refers to a saturated or unsaturated, branched, straight chain or cyclic hydrocarbon radical having two monovalent radical centers derived by the removal of one hydrogen atom from each of two different carbon atoms of a parent alkane, alkene, or alkyne.

"Aqueous solution" is to be understood as a solution containing water, even small amounts of water. For example, a solution containing 1% water is to be understood as an aqueous solution.

"Hybridization application," "hybridization assay," "hybridization experiment," "hybridization procedure," "hybridization technique," "hybridization method," etc. are to be understood as referring to any process that involves hybridization of nucleic acids. Such a process may include, for example, a fixation step, a deparaffination step, a heat-pretreatment step, a digestion step, denaturation and hybridization steps, a stringency wash step, and a mounting step. Unless otherwise specified, the terms "hybridization" and "hybridization step" are to be understood as referring to the re-annealing step of the hybridization procedure as well as the denaturation step.

"Hybridization composition" refers to an aqueous solution of the invention for performing a hybridization procedure, for example, to bind a probe to a nucleic acid sequence. Hybridization compositions may comprise, e.g., at least one polar aprotic solvent, at least one nucleic acid sequence, and a hybridization solution. Hybridization compositions do not comprise enzymes or other components, such as deoxynucleoside triphosphates (dNTPs), for amplifying nucleic acids in a biological sample.

"Hybridization solution" refers to an aqueous solution for use in a hybridization composition of the invention. Hybridization solutions are discussed in detail below and may comprise, e.g., buffering agents, accelerating agents, chelating agents, salts, detergents, and blocking agents.

"Hansen Solubility Parameters" and "HSP" refer to the following cohesion energy (solubility) parameters: (1) the dispersion solubility parameter ($\delta_D$, "D parameter"), which measures nonpolar interactions derived from atomic forces; (2) the polar solubility parameter ($\delta_P$, "P parameter"), which measures permanent dipole-permanent dipole interactions; and (3) the hydrogen bonding solubility parameter ($\delta_H$, "H parameter"), which measures electron exchange. The Hansen Solubility Parameters are further defined below.

"Repetitive Sequences" is to be understood as referring to the rapidly reannealing (approximately 25%) and/or intermediately reannealing (approximately 30%) components of mammalian genomes. The rapidly reannealing components contain small (a few nucleotides long) highly repetitive sequences usually found in tandem (e.g., satellite DNA), while the intermediately reannealing components contain interspersed repetitive DNA. Interspersed repeated sequences are classified as either SINEs (short interspersed repeat sequences) or LINEs (long interspersed repeated sequences), both of which are classified as retrotransposons in primates. SINEs and LINEs include, but are not limited to, Alu-repeats, Kpn-repeats, di-nucleotide repeats, tri-nucleotide repeats, tetra-nucleotide repeats, penta-nucleotide repeats and hexa-nucleotide repeats. Alu repeats make up the majority of human SINEs and are characterized by a consensus sequence of approximately 280 to 300 bp that consist of two similar sequences arranged as a head to tail dimer. In addition to SINEs and LINEs, repeat sequences also exist in chromosome telomeres at the termini of chromosomes and chromosome centromeres, which contain distinct repeat sequences that exist only in the central region of a chromosome. However, unlike SINEs and LINEs, which are dispersed randomly throughout the entire genome, telomere and centromere repeat sequences are localized within a certain region of the chromosome.

"Non-toxic" and "reduced toxicity" are defined with respect to the toxicity labeling of formamide according to "Directive 1999/45/EC of the European Parliament and of the Council of 31 May 1999 concerning the approximation of the laws, regulations and administrative provisions of the Member States relating to the classification, packaging, and labelling of dangerous preparations" (ecb.jrc.it/legislation/1999L0045EC.pdf) ("Directive"). According to the Directive, toxicity is defined using the following classification order: T+ "very toxic"; T "toxic", C "corrosive", Xn "harmful", Xi "irritant." Risk Phrases ("R phrases") describe the risks of the classified toxicity. Formamide is listed as T (toxic) and R61 (may cause harm to the unborn child). All of the following chemicals are classified as less toxic than formamide: acetonitrile (Xn, R11, R20, R21, R22, R36); sulfolane (Xn, R22); γ-butyrolactone (Xn, R22, R32); and ethylene carbonate (Xi, R36, R37, R38). At the time of filing this application, ethylene trithiocarbonate and glycol sulfite are not presently labeled.

"Stringent" and "stringency" in the context of post-hybridization washes are to be understood as referring to conditions for denaturing non-complementary base-pairing. In general, a signal to noise ratio of 2× (or higher) than that observed for an unrelated probe in the particular hybridization assay indicates specific hybridization with little non-complementary base-pairing.

Stringent wash conditions are sequence dependent and are different under different environmental parameters. The melting temperature ($T_m$) can be used to adjust wash conditions to increase complementary base pairing. $T_m$ is the temperature (under defined ionic strength and pH) at which 50% of the target sequence hybridizes to a perfectly matched probe. For DNA-DNA hybrids, the $T_m$ can be approximated from the following equation:

$$T_m = 81.5° \text{C.} + 16.6(\log M) + 0.41(\% \ GC) - 0.61(\% \ \text{form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching. Accordingly, stringent conditions are generally selected to be about 5° C. lower than $T_m$ for the specific sequence and its complement at a defined ionic strength and pH. However, severely stringent conditions can utilize a wash at 1, 2, 3, or 4° C. lower than $T_m$; moderately stringent conditions can utilize a wash at 6, 7, 8, 9, or 10° C. lower than $T_m$; low stringency conditions can utilize a wash at 11, 12, 13, 14, 15, or 20° C. lower than $T_m$. Using the equation, those of ordinary skill will understand that variations in the stringency of wash solutions are inherently described.

As used herein, the terms "room temperature" and "RT" refer to about 20° C. to about 25° C., unless otherwise stated.

B. Solvent Selection

Suitable polar aprotic solvents for use in the invention may be selected based on their Hansen Solubility Parameters. Methods for experimentally determining and/or calculating HSP for a solvent are known in the art, and HSP have been reported for over 1200 chemicals.

For example, the D parameter may be calculated with reasonable accuracy based on refractive index, or may be derived from charts by comparison with known solvents of similar size, shape, and composition after establishing a critical temperature and molar volume. The P parameter may be estimated from known dipole moments (see, e.g., McClellan A. L., Tables of Experimental Dipole Moments (W.H. Freeman 1963)) using Equation 1:

$$\delta_P = 37.4(\text{Dipole Moment})/V^{1/2} \qquad \text{Equation 1}$$

where V is the molar volume. There are no equations for calculating the H parameter. Instead, the H parameter is usually determined based on group contributions. HSP characterizations are conveniently visualized using a spherical representation, with the HSP of an experimentally-determined suitable reference solvent at the center of the sphere. The radius of the sphere (R) indicates the maximum tolerable variation from the HSP of the reference solvent that still allows for a "good" interaction to take place. Good solvents are within the sphere and bad ones are outside. The distance, $R_a$, between two solvents based on their respective HSP values can be determined using Equation 2:

$$(R_a)^2 = 4(\delta_{D1} - \delta_{D2})^2 + (\delta_{P1} - \delta_{P2})^2 (\delta_{H1} - \delta_{H2})^2 \qquad \text{Equation 2}$$

where subscript 1 indicates the reference sample, subscript 2 indicates the test chemical, and all values are in $\text{MPa}^{1/2}$. Good solubility requires that $R_a$ be less than the experimentally-determined radius of the solubility sphere $R_o$. The relative energy difference between two solvents, i.e., RED number, can be calculated by taking the ratio of $R_a$ to $R_o$, as shown in Equation 3.

$$\text{RED} = R_a/R_o \qquad \text{Equation 3}$$

RED numbers less than 1.0 indicate high affinity; RED numbers equal or close to 1.0 indicate boundary conditions; and progressively higher RED numbers indicate progressively lower affinities.

In some embodiments, the D parameters of the polar aprotic solvents of the invention are between 17.7 to 22.0 MPa$^{1/2}$. Such relatively high D parameters are generally associated with solvents having cyclic structures and/or structures with sulfur or halogens. Linear compounds are not likely to be among the most suitable polar aprotic solvents for use in the invention, but may be considered if their P and H parameters are within the ranges discussed below. Since the D parameter is multiplied by 4 in Equation 2, the limits are one-half of $R_o$. In addition, it should be noted that D values of around 21 or higher are often characteristic of a solid.

In some embodiments, the P parameters of the polar aprotic solvents of the invention are between 13 to 23 MPa$^{1/2}$. Such exceptionally high P parameters are generally associated with solvents having a high dipole moment and presumably also a relatively low molecular volume. For example, for V near 60 cc/mole, the dipole moment should be between 4.5 and 3.1. For V near 90 cc/mole, the dipole moment should be between 5.6 and 3.9.

In some embodiments, the H parameters of the polar aprotic solvents of the invention are between 3 to 13 MPa$^{1/2}$. Generally, polar aprotic solvents having an alcohol group are not useful in the compositions and methods of the invention, since the H parameters of such solvents would be too high.

The molar volume of the polar aprotic solvent may also be relevant, since it enters into the evaluation of all three Hansen Solubility Parameters. As molar volume gets smaller, liquids tend to evaporate rapidly. As molar volume gets larger, liquids tend to enter the solid region in the range of D and P parameters recited above. Thus, the polar aprotic solvents of the invention are rather close to the liquid/solid boundary in HSP space.

In some embodiments, the polar aprotic solvents of the invention have lactone, sulfone, nitrile, sulfite, and/or carbonate functionality. Such compounds are distinguished by their relatively high dielectric constants, high dipole moments, and solubility in water. An exemplary polar aprotic solvent with lactone functionality is γ-butyrolactone (GBL), an exemplary polar aprotic solvent with sulfone functionality is sulfolane (SL; tetramethylene sulfide-dioxide), an exemplary polar aprotic solvent with nitrile functionality is acetonitrile (AN), an exemplary polar aprotic solvent with sulfite functionality is glycol sulfite/ethylene sulfite (GS), and an exemplary polar aprotic solvents with carbonate functionality are ethylene carbonate (EC), propylene carbonate (PC), or ethylene trithiocarbonate (ETC). The structures of these exemplary solvents are provided below and their Hansen Solubility Parameters, RED numbers, and molar volumes are given in Table 1.

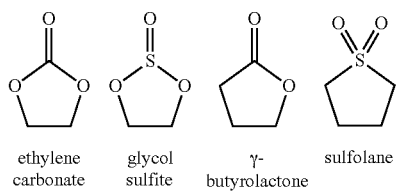

ethylene carbonate  glycol sulfite  γ-butyrolactone  sulfolane

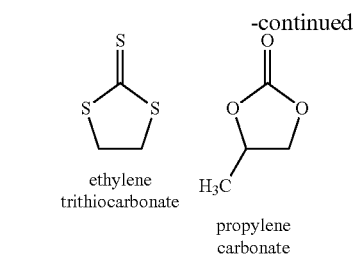

ethylene trithiocarbonate   propylene carbonate

TABLE 1

|  | D | P | H | RED | Molar Volume (cm³/mole) |
|---|---|---|---|---|---|
| Correlation ($R_0$ = 3.9) | 19.57 | 19.11 | 7.71 | — | — |
| GBL | 19.0 | 16.6 | 7.4 | 0.712 | 76.5 |
| PC | 20.0 | 18.0 | 4.1 | 0.993 | 85.2 |
| SL | 20.3 | 18.2 | 10.9 | 0.929 | 95.7 |
| EC | 19.4 | 21.7 | 5.1 | 0.946 | 66.0 |
| ETC | n/a | n/a | n/a | n/a | n/a |
| GS | 20.0 | 15.9 | 5.1 | n/a | 75.1 | n/a = not available.

Other suitable polar aprotic solvents that may be used in the invention are cyclic compounds such as, e.g., ε-caprolactone. In addition, substituted pyrrolidinones and related structures with nitrogen in a 5- or 6-membered ring, and cyclic structures with two nitrile groups, or one bromine and one nitrile group, may also be suitable for use in the invention. For example, N-methylpyrrolidinone (shown below) may be a suitable polar aprotic solvent for use in the methods and compositions of the invention.

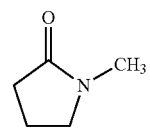

Other suitable polar aprotic solvents may contain a ring urethane group (NHCOO—). However, not all such compounds are suitable. One of skill in the art may screen for compounds useful in the compositions and methods of the invention as described herein. Exemplary chemicals that may be suitable for use in the invention are set forth in Tables 2 and 3 below.

TABLE 2

| Solvent | D | P | H |
|---|---|---|---|
| Acetanilide | 20.6 | 13.3 | 12.4 |
| N-Acetyl Pyrrolidone | 17.8 | 13.1 | 8.3 |
| 4-Amino Pyridine | 20.4 | 16.1 | 12.9 |
| Benzamide | 21.2 | 14.7 | 11.2 |
| Benzimidazole | 20.6 | 14.9 | 11.0 |
| 1,2,3-Benzotriazole | 18.7 | 15.6 | 12.4 |
| Butadienedioxide | 18.3 | 14.4 | 6.2 |
| 2,3-Butylene Carbonate | 18.0 | 16.8 | 3.1 |
| Caprolactone (Epsilon) | 19.7 | 15.0 | 7.4 |
| Chloro Maleic Anhydride | 20.4 | 17.3 | 11.5 |
| 2-Chlorocyclohexanone | 18.5 | 13.0 | 5.1 |
| Chloronitromethane | 17.4 | 13.5 | 5.5 |
| Citraconic Anhydride | 19.2 | 17.0 | 11.2 |
| Crotonlactone | 19.0 | 19.8 | 9.6 |

TABLE 2-continued

| Solvent | D | P | H |
|---|---|---|---|
| Cyclopropylnitrile | 18.6 | 16.2 | 5.7 |
| Dimethyl Sulfate | 17.7 | 17.0 | 9.7 |
| Dimethyl Sulfone | 19.0 | 19.4 | 12.3 |
| Dimethyl Sulfoxide | 18.4 | 16.4 | 10.2 |
| 1,2-Dinitrobenzene | 20.6 | 22.7 | 5.4 |
| 2,4-Dinitrotoluene | 20.0 | 13.1 | 4.9 |
| Dipheynyl Sulfone | 21.1 | 14.4 | 3.4 |
| 1,2-Dinitrobenzene | 20.6 | 22.7 | 5.4 |
| 2,4-Dinitrotoluene | 20.0 | 13.1 | 4.9 |
| Epsilon-Caprolactam | 19.4 | 13.8 | 3.9 |
| Ethanesulfonylchloride | 17.7 | 14.9 | 6.8 |
| Furfural | 18.6 | 14.9 | 5.1 |
| 2-Furonitrile | 18.4 | 15.0 | 8.2 |
| Isoxazole | 18.8 | 13.4 | 11.2 |
| Maleic Anhydride | 20.2 | 18.1 | 12.6 |
| Malononitrile | 17.7 | 18.4 | 6.7 |
| 4-Methoxy Benzonitrile | 19.4 | 16.7 | 5.4 |
| 1-Methoxy-2-Nitrobenzene | 19.6 | 16.3 | 5.5 |
| 1-Methyl Imidazole | 19.7 | 15.6 | 11.2 |
| 3-Methyl Isoxazole | 19.4 | 14.8 | 11.8 |
| N-Methyl Morpholine-N-Oxide | 19.0 | 16.1 | 10.2 |
| Methyl Phenyl Sulfone | 20.0 | 16.9 | 7.8 |
| Methyl Sulfolane | 19.4 | 17.4 | 5.3 |
| Methyl-4-Toluenesulfonate | 19.6 | 15.3 | 3.8 |
| 3-Nitroaniline | 21.2 | 18.7 | 10.3 |
| 2-Nitrothiophene | 19.7 | 16.2 | 8.2 |
| 9,10-Phenanthrenequinone | 20.3 | 17.1 | 4.8 |
| Phthalic Anhydride | 20.6 | 20.1 | 10.1 |
| 1,3-Propane Sultone | 18.4 | 16.0 | 9.0 |
| beta-Propiolactone | 19.7 | 18.2 | 10.3 |
| 2-Pyrrolidone | 19.4 | 17.4 | 11.3 |
| Saccharin | 21.0 | 13.9 | 8.8 |
| Succinonitrile | 17.9 | 16.2 | 7.9 |
| Sulfanilamide | 20.0 | 19.5 | 10.7 |
| Sulfolane | 20.3 | 18.2 | 10.9 |
| 2,2,6,6-Tetrachlorocyclohexanone | 19.5 | 14.0 | 6.3 |
| Thiazole | 20.5 | 18.8 | 10.8 |
| 3,3,3-Trichloro Propene | 17.7 | 15.5 | 3.4 |
| 1,1,2-Trichloro Propene | 17.7 | 15.7 | 3.4 |
| 1,2,3-Trichloro Propene | 17.8 | 15.7 | 3.4 |

Table 2 sets forth an exemplary list of potential chemicals for use in the compositions and methods of the invention based on their Hansen Solubility Parameters. Other compounds, may of course, also meet these requirements such as, for example, those set forth in Table 3.

TABLE 3

| Chemical (dipole moment) | RED | Melting Point ° C. |
|---|---|---|
| Chloroethylene carbonate (4.02) | 0.92 | — |
| 2-Oxazolidinone (5.07) | 0.48 | 86-89 |
| 2-Imidazole | 1.49 | 90-91 |
| 1,5-Dimethyl Tetrazole (5.3) | ~1.5 | 70-72 |
| N-Ethyl Tetrazole (5.46) | ~1.5 | — |
| Trimethylene sulfide-dioxide (4.49) | — | — |
| Trimethylene sulfite (3.63) | — | — |
| 1,3-Dimethyl-5-Tetrazole (4.02) | — | — |
| Pyridazine (3.97) | 1.16 | −8 |
| 2-Thiouracil (4.21) | — | — |
| N-Methyl Imidazole (6.2) | 1.28 | — |
| 1-Nitroso-2-pyrolidinone | ~1.37 | — |
| Ethyl Ethyl Phosphinate (3.51) | — | — |
| 5-cyano-2-Thiouracil (5.19) | — | — |
| 4H-Pyran-4-thione (4.08) | 1.35 | 32-34 |
| 4H-Pyran-4-one = gamma pyrone (4.08) | 1.49 | Boiling Point (BP) 80 |
| 2-Nitrofuran (4.41) | 1.14 | 29 |
| Methyl alpha Bromo Tetronate (6.24) | — | — |
| Tetrahydrothiapyran oxide (4.19) | 1.75 | 60-64 |
| Picolinonitrile (2-cyanopyridine) (5.23) | 0.40 | 26-28 (BP 212-215) |
| Nitrobenzimidazole (6.0) | 0.52 | 207-209 |
| Isatin (5.76) | — | 193-195 |

TABLE 3-continued

| Chemical (dipole moment) | RED | Melting Point ° C. |
|---|---|---|
| N-phenyl sydnone (6.55) | — | — |
| Glycol sulfate (Ethylene glycol) | — | 99° C. |
| Note: not soluble at 40% | | |

Some of the chemicals listed in Tables 2 and 3 have been used in hybridization and/or PCR applications in the prior art (e.g., dimethyl sulfoxide (DMSO) has been used in hybridization and PCR applications, and sulfolane (SL), acetonitrile (AN), 2-pyrrolidone, ϵ-caprolactam, and ethylene glycol have been used in PCR applications). Thus, in some embodiments, the polar aprotic solvent is not DMSO, sulfolane, acetonitrile, 2-pyrrolidone, ϵ-caprolactam, or ethylene glycol. However, most polar aprotic solvents have not been used in prior art hybridization applications. Moreover, even when such compounds were used, the prior art did not recognize that they may be advantageously used in the stringent wash step of such hybridization applications, as disclosed in this application.

In addition, not all of the chemicals listed in Tables 2 and 3 are suitable for use in the compositions and methods of the invention. For example, although DMSO is listed in Table 2 because its Hansen Solubility Parameters (HSPs) fall within the ranges recited above, DMSO likely does not function in the stringent wash compositions and methods of the invention. However, it is well within the skill of the ordinary artisan to screen for suitable compounds using the guidance provided herein including testing a compound in one of the examples provided. For example, in some embodiments, suitable polar aprotic solvents will have HSPs within the ranges recited above and a structure shown in Formulas 1-9 above.

C. Compositions, Buffers, and Solutions (1) Stringent Wash Solutions

Traditional stringent wash solutions are known in the art. Such solutions may comprise, for example, buffering agents, accelerating agents, chelating agents, salts, detergents, and blocking agents.

For example, the buffering agents may include SSC, HEPES, SSPE, PIPES, TMAC, TRIS, SET, citric acid, a phosphate buffer, such as, e.g., potassium phosphate or sodium pyrrophosphate, etc. The buffering agents may be present at concentrations from 0.01× to 50×, such as, for example, 0.01×, 0.1×, 0.5×, 1×, 2×, 5×, 10×, 15×, 20×, 25×, 30×, 35×, 40×, 45×, or 50×. Typically, the buffering agents are present at concentrations from 0.1× to 10×.

The accelerating agents may include polymers such as FICOLL, PVP, heparin, dextran sulfate, proteins such as BSA, glycols such as ethylene glycol, glycerol, 1,3 propanediol, propylene glycol, or diethylene glycol, combinations thereof such as Dernhardt's solution and BLOTTO, and organic solvents such as formamide, dimethylformamide, DMSO, etc. The accelerating agent may be present at concentrations from 1% to 80% or 0.1× to 10×, such as, for example, 0.1% (or 0.1×), 0.2% (or 0.2×), 0.5% (or 0.5×), 1% (or 1×), 2% (or 2×), 5% (or 5×), 10% (or 10×), 15% (or 15×), 20% (or 20×), 25% (or 25×), 30% (or 30×), 40% (or 40×), 50% (or 50×), 60% (or 60×), 70% (or 70×), or 80% (or 80×). Typically, formamide is present at concentrations from 25% to 75%, such as 25%, 30%, 40%, 50%, 60%, 70%, or 75%, while DMSO, dextran sulfate, and glycol are present at concentrations from 5% to 10%, such as 5%, 6%, 7%, 8%, 9%, or 10%.

The chelating agents may include EDTA, EGTA, etc. The chelating agents may be present at concentrations from 0.1 mM to 10 mM, such as 0.1 mM, 0.2 mM, 0.5 mM, 1 mM, 2 mM, 3 mM, 4 mM, 5 mM, 6 mM, 7 mM, 8 mM, 9 mM, or 10 mM. Typically, the chelating agents are present at concentrations from 0.5 mM to 5 mM, such as 0.5 mM, 1 mM, 1.5 mM, 2 mM, 2.5 mM, 3 mM, 3.5 mM, 4 mM, 4.5 mM, or 5 mM.

The salts may include sodium chloride, sodium phosphate, magnesium phosphate, etc. The salts may be present at concentrations from 1 mM to 750 mM, such as 1 mM, 5 mM, 10 mM, 20 mM, 30 mM, 40 mM, 50 mM, 100 mM, 200 mM, 300 mM, 400 mM, 500 mM, 600 mM, 700 mM, or 750 mM. Typically, the salts are present at concentrations from 10 mM to 500 mM, such as 10 mM, 20 mM, 30 mM, 40 mM, 50 mM, 100 mM, 200 mM, 300 mM, 400 mM, or 500 mM.

The detergents may include Tween, SDS, Triton, CHAPS, deoxycholic acid, etc. The detergent may be present at concentrations from 0.001% to 10%, such as, for example, 0.0001, 0.01, 0.1, 0.5, 1, 2, 3, 4, 5, 6, 7, 8, 9, or 10%. Typically, the detergents are present at concentrations from 0.01% to 1%, such as 0.01%, 0.02%, 0.03%, 0.05%, 0.1%, 0.2%, 0.3%, 0.4%, 0.5%, 0.6%, 0.7%, 0.8%, 0.9%, or 1%.

A great variation exists in the literature regarding traditional hybridization wash solutions. For instance, an example of a typical stringent wash is 1×SSC (20×SSC=3M NaCl, 0.3M trisodium citrate, pH 7.0) at 65° C. for 10 minutes. Another example of a typical stringent wash is: first a high stringency wash with 0.4× (or 1×) SSC, 0.3% NP-40, pH 7.0 at 73° C. for 2 min., followed by a medium stringency wash with 2×SSC, 0.1% NP-40, pH 7.0 at room temperature for 1-10 min. For example, a typical stringent wash for nucleic acids which have more than 100 complementary residues is a 0.1× to 0.2×SSC at 60 to 65° C. for 15 minutes. An example a typical medium stringency wash for nucleic acids which have more than 100 complementary residues is 0.5× to 1×SSC at 45 to 55° C. for 15 minutes. An example a typical low stringency wash for nucleic acids which have more than 100 complementary residues is 2× to 5×SSC at 40 to 50° C. for 15 minutes. For shorter probes (e.g., about 10 to 50 nucleotides), stringent conditions typically involve salt concentrations of less than about 1.5 M, more typically about 0.01 to 1.0 M, at pH 7.0 to 8.3, and the temperature is typically at least about 30° C.

Stringent conditions may also be achieved with the addition of destabilizing agents such as formamide. For instance, for post hybridization washes of single locus FISH with large DNA probes based on, e.g., BAC and Cosmid clones hybridized at 37° C.: stringent washes may use 2×SSC and 50% formamide for 3×5 min from 42 to 45° C. In addition, stringent conditions with formamide may be optimized for different types and lengths of probes (e.g. DNA oligos; LNA; PNA) and different targets (e.g. mRNA, virus).

The compositions of the invention may comprise a wash solution comprising any of the components of traditional components recited above in combination with at least one polar aprotic solvent. The traditional components may be present at the same concentrations as used in traditional wash solutions, or may be present at higher or lower concentrations, or may be omitted completely.

For example, if the compositions of the invention comprise salts such as NaCl and/or phosphate buffer, the salts may be present at concentrations of 0-1200 mM NaCl and/or 0-200 mM phosphate buffer. In some embodiments, the concentrations of salts may be, for example, 0 mM, 15 mM, 30 mM, 45 mM, 60 mM, 75 mM, 90 mM, 105 mM, 120 mM, 135 mM, 150 mM, 165 mM, 180 mM, 195 mM, 210 mM, 225 mM, 240 mM, 255 mM, 270 mM, 285 mM, or 300 mM NaCl and 5 mM phosphate buffer, or 600 mM NaCl and 10 mM phosphate buffer. In other embodiments, the concentrations of salts may be, for example, the concentrations present in 0.1×, 0.2×, 0.3×, 0.4×, 0.5×, 0.6×, 0.7×, 0.8×, 0.9×, 1×, 2×, 3×, 4×, 5×, 6×, 7×, or 8×SSC.

If the compositions of the invention comprise accelerating agents such as dextran sulfate, glycol, or DMSO, the dextran sulfate may be present at concentrations of from 5% to 40%, the glycol may be present at concentrations of from 0.1% to 10%, and the DMSO may be from 0.1% to 10%. In some embodiments, the concentration of dextran sulfate may be 10% or 20% and the concentration of ethylene glycol, 1,3 propanediol, or glycerol may be 1% to 10%. In some embodiments, the concentration of DMSO may be 1%. In some embodiments, the aqueous composition does not comprise DMSO as an accelerating agent. In some embodiments, the aqueous composition does not comprise formamide as an accelerating agent, or comprises formamide with the proviso that the composition contains less than 25%, or less than 10%, or less than 5%, or less than 2%, or less than 1%, or less than 0.5%, or less than 0.1%, or less than 0.05%, or less than 0.01%.

If the compositions of the invention comprise citric acid, the concentrations may range from 1 mM to 100 mM and the pH may range from 5.0 to 8.0. In some embodiments the concentration of citric acid may be 10 mM and the pH may be 6.2.

The compositions of the invention may comprise agents that reduce non-specific binding to, for example, the cell membrane, such as salmon sperm or small amounts of total human DNA or, for example, they may comprise blocking agents to block binding of, e.g., repeat sequences to the target such as larger amounts of total human DNA or repeat enriched DNA or specific blocking agents such as PNA or LNA fragments and sequences. These agents may be present at concentrations of from 0.01-100 µg/µL or 0.01-100 µM. For example, in some embodiments, these agents will be 0.1 µg/µL total human DNA, or 0.1 µg/µL non-human DNA, such as herring sperm, salmon sperm, or calf thymus DNA, or 5 µM blocking PNA.

One aspect of the invention is a composition or solution for use in a stringent wash step in a hybridization application. Compositions for use in the invention include an aqueous composition comprising at least one polar aprotic solvent in an amount effective to denature non-complementary double-stranded nucleotide sequences. One way to test for whether the amount of polar aprotic solvent is effective to denature non-complementary sequences in a hybridization product is to determine whether the polar aprotic solvent, when used in the methods and compositions described herein, yields a signal to noise ratio of 2× (or higher) than that observed for an unrelated probe in the particular hybridization assay.

Non-limiting examples of effective amounts of polar aprotic solvents include, e.g., about 1% to about 95% (v/v). In some embodiments, the concentration of polar aprotic solvent is 5% to 60% (v/v). In other embodiments, the concentration of polar aprotic solvent is 10% to 60% (v/v). In still other embodiments, the concentration of polar aprotic solvent is 30% to 50% (v/v). Concentrations of 1% to 5%, 5% to 10%, 10%, 10% to 20%, 20% to 30%, 30% to 40%, 40% to 50%, or 50% to 60% (v/v) are also suitable. In some embodiments, the polar aprotic solvent will be present at a concentration of 0.1%, 0.25%, 0.5%, 1%, 2%, 3%, 4%, or 5% (v/v). In other embodiments, the polar aprotic solvent will be present at a concentration of 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v).

In one embodiment, a composition of the invention comprises a mixture of 20% polar aprotic solvent (v/v) (e.g., ethylene carbonate, "EC") and 2×SSC at pH 7.0. Another exemplary composition of the present invention comprises a mixture of 50% EC and 2×SSC at pH 7.0.

(2) Polar Aprotic Solvent(s)

Different polar aprotic solvents may impart different properties on the compositions of the invention. For example, the choice of polar aprotic solvent may contribute to the stability of the composition, since certain polar aprotic solvents may degrade over time. For example, the polar aprotic solvent ethylene carbonate breaks down into ethylene glycol, which is a relatively stable molecule, and carbon dioxide, which can interact with water to form carbonic acid, altering the acidity of the compositions of the invention. Without being bound by theory, it is believed that the change in pH upon breakdown of ethylene carbonate and DNA damage from long storage makes the compositions of the invention less effective. However, stability can be improved by reducing the pH of the composition, by adding citric acid as a buffer at pH 6.2 instead of the traditional phosphate buffer, which is typically used at about pH 7.4, and/or by adding ethylene glycol at concentrations, e.g., between 0.1% to 10%, or between 0.5% to 5%, such as, for example, 1%, 2%, 3%, etc. For example, with 10 mM citrate buffer, the compositions of the invention are stable at 2-8° C. for approximately 8 months. Stability can also be improved if the compositions are stored at low temperatures (e.g., −20° C.).

In addition, certain polar aprotic solvents may cause the compositions of the invention to separate into multi-phase systems under certain conditions. The conditions under which multi-phase systems are obtained may be different for different polar aprotic solvents. Generally, however, as the concentration of polar aprotic solvent increases, the number of phases increases. For example, compositions comprising low concentrations ethylene carbonate (i.e., less than 20%) may exist as one phase, while compositions comprising higher concentrations of ethylene carbonate may separate into two, or even three phases. For instance, compositions comprising 15% ethylene carbonate exist as a single phase at room temperature, while compositions comprising 40% ethylene carbonate consist of a viscous lower phase (approximately 25% of the total volume) and a less viscous upper phase (approximately 75% of the total volume) at room temperature. On the other hand, compositions comprising greater than 20% EC, for example 40% or 50% EC, and 2×SSC may be present as a single phase at room temperature.

On the other hand, some polar aprotic solvents may exist in two phases at room temperature even at low concentrations. For example, sulfolane, γ-butyrolactone, ethylene trithiocarbonate, glycol sulfite, and propylene carbonate exist as two phases at concentrations of 10, 15, 20, or 25% (20% dextran sulfate, 600 mM NaCl, 10 mM citrate buffer) at room temperature.

It may also be possible to alter the number of phases by adjusting the temperature of the compositions of the invention. Generally, as temperature increases, the number of phases decreases. For example, at 2-8° C., compositions comprising 40% ethylene carbonate may separate into a three-phase system.

It may also be possible to alter the number of phases if present in the compositions by adjusting the concentration of salt in the composition. Generally speaking, lowering the salt concentration may reduce the number of phases. However, depending on the particular polar aprotic solvent and its concentration in the composition, single phases may be produced even with higher concentrations of salt.

Washes may be performed with a one-phase composition of the invention, with individual phases of the multiphase compositions of the invention, or with mixtures of any one or more of the phases in a multiphase composition of the invention.

(3) Optimization for Particular Applications

The compositions of the invention can be varied in order to optimize results for a particular application. For example, the concentration of polar aprotic solvent, salt, accelerating agent, blocking agent, and/or hydrogen ions (i.e. pH) may be varied in order to improve results for a particular application. For example, the concentration of polar aprotic solvent may be varied in order to improve signal intensity and background staining.

D. Applications, Methods, and Uses (1) Analytical Samples

The methods and compositions of the invention may be used fully or partly in all types of hybridization applications in the fields of cytology, histology, or molecular biology. According to one embodiment, the first or the second nucleic acid sequence in the methods of the invention is present in a biological sample. Examples of such samples include, e.g., tissue samples, cell preparations, cell fragment preparations, and isolated or enriched cell component preparations. The sample may originate from various tissues such as, e.g., breast, lung, colorectal, prostate, lung, head & neck, stomach, pancreas, esophagus, liver, and bladder, or other relevant tissues and neoplasia thereof, any cell suspension, blood sample, fine needle aspiration, ascites fluid, sputum, peritoneum wash, lung wash, urine, feces, cell scrape, cell smear, cytospin or cytoprep cells.

The sample may be isolated and processed using standard protocols. Cell fragment preparations may, e.g., be obtained by cell homogenizing, freeze-thaw treatment or cell lysing. The isolated sample may be treated in many different ways depending of the purpose of obtaining the sample and depending on the routine at the site. Often the sample is treated with various reagents to preserve the tissue for later sample analysis, alternatively the sample may be analyzed directly. Examples of widely used methods for preserving samples are formalin-fixed followed by paraffin-embedding and cryo-preservation.

For metaphase spreads, cell cultures are generally treated with colcemid, or anther suitable spindle pole disrupting agent, to stop the cell cycle in metaphase. The cells are then fixed and spotted onto microscope slides, treated with formaldehyde, washed, and dehydrated in ethanol. Probes are then added and the samples are analyzed by any of the techniques discussed below.

Cytology involves the examination of individual cells and/or chromosome spreads from a biological sample. Cytological examination of a sample begins with obtaining a specimen of cells, which can typically be done by scraping, swabbing or brushing an area, as in the case of cervical specimens, or by collecting body fluids, such as those obtained from the chest cavity, bladder, or spinal column, or by fine needle aspiration or fine needle biopsy, as in the case of internal tumors. In a conventional manual cytological preparation, the sample is transferred to a liquid suspending material and the cells in the fluid are then transferred directly or by centrifugation-based processing steps onto a glass microscope slide for viewing. In a typical automated cytological preparation, a filter assembly is placed in the liquid suspension and the filter assembly both disperses the cells and captures the cells on the filter. The filter is then removed and placed in contact with a microscope slide. The cells are then fixed on the microscope slide before analysis by any of the techniques discussed below.

In a traditional DNA hybridization experiment using a cytological sample, slides containing the specimen are immersed in a formaldehyde buffer, washed, and then dehydrated in ethanol. The probes are then added and the specimen is covered with a coverslip. The slide is optionally incubated at a temperature sufficient to denature any double-stranded nucleic acid in the specimen (e.g., 5 minutes at 82° C.) and then incubated at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

In a traditional RNA hybridization experiment using cytological samples, cells are equilibrated in 40% formamide, 1×SSC, and 10 mM sodium phosphate for 5 min, incubated at 37° C. overnight in hybridization reactions containing 20 ng of oligonucleotide probe (e.g mix of labeled 50 bp oligos), 1×SSC, 40% formamide, 10% dextran sulfate, 0.4% BSA, 20 mM ribonucleotide vanadyl complex, salmon testes DNA (10 mg/ml), *E. coli* tRNA (10 mg/ml), and 10 mM sodium phosphate. Then washed twice with 4×SSC/40% formamide and again twice with 2×SSC/40% formamide, both at 37° C., and then with 2×SSC three times at room temperature. Digoxigenin-labeled probes can then e.g. be detected by using a monoclonal antibody to digoxigenin conjugated to Cy3. Biotin-labeled probes can then e.g. be detected by using streptavidin-Cy5. Detection can be by fluorescence or CISH.

Histology involves the examination of cells in thin slices of tissue. To prepare a tissue sample for histological examination, pieces of the tissue are fixed in a suitable fixative, typically an aldehyde such as formaldehyde or glutaraldehyde, and then embedded in melted paraffin wax. The wax block containing the tissue sample is then cut on a microtome to yield thin slices of paraffin containing the tissue, typically from 2 to 10 microns thick. The specimen slice is then applied to a microscope slide, air dried, and heated to cause the specimen to adhere to the glass slide. Residual paraffin is then dissolved with a suitable solvent, typically xylene, toluene, or others. These so-called deparaffinizing solvents are then removed with a washing-dehydrating type reagent prior to analysis of the sample by any of the techniques discussed below. Alternatively, slices may be prepared from frozen specimens, fixed briefly in 10% formalin or other suitable fixative, and then infused with dehydrating reagent prior to analysis of the sample.

In a traditional DNA hybridization experiment using a histological sample, formalin-fixed paraffin embedded tissue specimens are cut into sections of 2-6 μm and collected on slides. The paraffin is melted (e.g., 30-60 minutes at 60° C.) and then removed (deparaffinated) by washing with xylene (or a xylene substitute), e.g., 2×5 minutes. The samples are rehydrated, washed, and then pre-treated (e.g., 10 minutes at 95-100° C.). The slides are washed and then treated with pepsin or another suitable permeabilizer, e.g., 3-15 minutes at 37° C. The slides are washed (e.g., 2×3 minutes), dehydrated, and probe is applied. The specimens are covered with a coverslip and the slide is optionally incubated at a temperature sufficient to denature any double-stranded nucleic acid in the specimen (e.g. 5 minutes at 82° C.), followed by incubation at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

In a traditional RNA hybridization experiment using a histological sample, slides with FFPE tissue sections are deparaffinized in xylene for 2×5 min, immerged in 99% ethanol 2×3 min, in 96% ethanol 2×3 min, and then in pure water for 3 min. Slides are placed in a humidity chamber, Proteinase K is added, and slides are incubated at RT for 5 min-15 min. Slides are immersed in pure water for 2×3 min, immersed in 96% ethanol for 10 sec, and air-dried for 5 min. Probes are added to the tissue section and covered with coverslip. The slides are incubated at 55° C. in humidity chamber for 90 min. After incubation, the slides are immersed in a Stringent Wash solution at 55° C. for 25 min, and then immersed in TBS for 10 sec. The slides are incubated in a humidity chamber with antibody for 30 min. The slides are immersed in TBS for 2×3 min, then in pure water for 2×1 min, and then placed in a humidity chamber. The slides are then incubated with substrate for 60 min, and immersed in tap water for 5 min.

In a traditional northern blot procedure, the RNA target sample is denatured for 10 minutes at 65° C. in RNA loading buffer and immediately placed on ice. The gels are loaded and electrophoresed with 1×MOPS buffer (10×MOPS contains 200 mM morpholinopropansulfonic acid, 50 mM sodium acetate, 10 mM EDTA, pH 7.0) at 25 V overnight. The gel is then pre-equilibrated in 20×SSC for 10 min and the RNA is transferred to a nylon membrane using sterile 20×SSC as transfer buffer. The nucleic acids are then fixed on the membrane using, for example, UV-cross linking at 120 mJ or baking for 30 min at 120° C. The membrane is then washed in water and air dried. The membrane is placed in a sealable plastic bag and prehybridized without probe for 30 min at 68° C. The probe is denatured for 5 min at 100° C. and immediately placed on ice. Hybridization buffer (prewarmed to 68° C.) is added and the probe is hybridized at 68° C. overnight. The membrane is then removed from the bag and washed twice for 5 min each with shaking in a low stringency wash buffer (e.g., 2×SSC, 0.1% SDS) at room temperature. The membrane is then washed twice for 15 min each in prewarmed high stringency wash buffer (e.g., 0.1×SSC, 0.1% SDS) at 68° C. The membrane may then be stored or immediately developed for detection.

Additional examples of traditional hybridization techniques can be found, for example, in Sambrook et al., *Molecular Cloning A Laboratory Manual*, 2$^{nd}$ Ed., Cold Spring Harbor Laboratory Press, (1989) at sections 1.90-1.104, 2.108-2.117, 4.40-4.41, 7.37-7.57, 8.46-10.38, 11.7-11.8, 11.12-11.19, 11.38, and 11.45-11.57; and in Ausubel et al., *Current Protocols in Molecular Biology*, John Wiley & Sons, Inc. (1998) at sections 2.9.1-2.9.6, 2.10.4-2.10.5, 2.10.11-2.10.16, 4.6.5-4.6.9, 4.7.2-4.7.3, 4.9.7-4.9.15, 5.9.18, 6.2-6.5, 6.3, 6.4, 6.3.3-6.4.9, 5.9.12-5.9.13, 7.0.9, 8.1.3, 14.3.1-14.3.4, 14.9, 15.0.3-15.0.4, 15.1.1-15.1.8, and 20.1.24-20.1.25.

(2) Hybridization Techniques

The compositions and methods of the present invention can be used fully or partly in all types of nucleic acid hybridization techniques known in the art for cytological and histological samples. Such techniques include, for example, in situ hybridization (ISH), fluorescent in situ hybridization (FISH; including multi-color FISH, Fiber-FISH, etc.), chromogenic in situ hybridization (CISH), silver in situ hybridization (SISH), comparative genome hybridization (CGH), chromosome paints, and arrays in situ.

Molecular probes that are suitable for use in the methods of the invention may be directly or indirectly labeled with detectable compounds such as enzymes, chromophores, fluorochromes, and haptens. DNA probes may be present at concentrations of 0.1 to 100 ng/µL. For example, in some embodiments, the probes may be present at concentrations of 1 to 10 ng/µL. PNA probes may be present at concentrations of 0.5 to 5000 nM. For example, in some embodiments, the probes may be present at concentrations of 5 to 1000 nM.

Molecular probes that are suitable for use in the methods of the invention are described, e.g., in U.S. Patent Publication No. 2005/0266459, which is incorporated herein by reference. In general, probes may be prepared by chemical synthesis, PCR, or by amplifying a specific DNA sequence by cloning, inserting the DNA into a vector, and amplifying the vector an insert in appropriate host cells. Commonly used vectors include bacterial plasmids, cosmids, bacterial artificial chromosomes (BACs), PI diverted artificial chromosomes (PACs), or yeast artificial chromosomes (YACs). The amplified DNA is then extracted and purified for use as a probe. Methods for preparing and/or synthesizing probes are known in the art, e.g., as disclosed in PCT/US02/30573.

The nucleic acid probe may be a double or single stranded nucleic acid fragment or sequence, such as a DNA, RNA, or analogs such as PNA or LNA. The probes may be labeled to make identification of the probe-target hybrid possible by use, for example, of a fluorescence or bright field microscope/scanner. In some embodiments, the probe may be labeled using radioactive labels such as $^{31}$P, $^{33}$P, or $^{32}$S, non-radioactive labels such as digoxigenin and biotin, or fluorescent labels In general, the type of probe determines the type of feature one may detect in a hybridization assay. For example, total nuclear or genomic DNA probes can be used as a species-specific probe. Chromosome paints are collections of DNA sequences derived from a single chromosome type and can identify that specific chromosome type in metaphase and interphase nuclei, count the number of a certain chromosome, show translocations, or identify extra-chromosomal fragments of chromatin. Different chromosomal types also have unique repeated sequences that may be targeted for probe hybridization, to detect and count specific chromosomes. Large insert probes may be used to target unique single-copy sequences. With these large probes, the hybridization efficiency is inversely proportional to the probe size. Smaller probes can also be used to detect aberrations such as deletions, amplifications, inversions, duplications, and aneuploidy. For example, differently-colored locus-specific probes can be used to detect translocations via split-signal in situ hybridization.

In general, the ability to discriminate between closely related sequences is inversely proportional to the length of the hybridization probe because the difference in thermal stability decreases between wild type and mutant complexes as probe length increases. Probes of greater than 10 bp in length are generally required to obtain the sequence diversity necessary to correctly identify a unique organism or clinical condition of interest. On the other hand, sequence differences as subtle as a single base (point mutation) in very short oligomers (<10 base pairs) can be sufficient to enable the discrimination of the hybridization to complementary nucleic acid target sequences as compared with non-target sequences.

In one embodiment, at least one set of the in situ hybridization probes may comprise one or more PNA probes, as defined above and as described in U.S. Pat. No. 7,105,294, which is incorporated herein by reference. Methods for synthesizing PNA probes are described in PCT/US02/30573. Alternatively, or in addition, at least one set of the hybridization probes in any of the techniques discussed above may comprise one or more locked nucleic acid (LNA) probes, as described in WO 99/14226, which is incorporated herein by reference. Due to the additional bridging bond between the 2' and 4' carbons, the LNA backbone is pre-organized for hybridization. LNA/DNA and LNA/RNA interactions are stronger than the corresponding DNA/DNA and DNA/RNA interactions, as indicated by a higher melting temperature. Thus, the compositions and methods of the invention, which decrease the energy required for hybridization, are particularly useful for hybridizations with LNA probes.

In one embodiment, the probes may comprise a detectable label (a molecule that provides an analytically identifiable signal that allows the detection of the probe-target hybrid), as described in U.S. Patent Publication No. 2005/0266459, which is incorporated herein by reference. The detectable label may be directly attached to a probe, or indirectly attached to a probe, e.g., by using a linker. Any labeling method known to those in the art, including enzymatic and chemical processes, can be used for labeling probes used in the methods and compositions of the invention. In other embodiments, the probes are not labeled.

In general, in situ hybridization techniques such as FISH, CISH, and SISH for DNA detection, employ large, mainly unspecified, nucleic acid probes that hybridize with varying stringency. Using large probes renders the in situ hybridization technique very sensitive. However, the successful use of large probes in traditional hybridization assays depends on blocking the undesired background staining derived from, e.g., repetitive sequences that are present throughout the genome. Traditional methods for decreasing nonspecific probe binding include saturating the binding sites on proteins and tissue by incubating tissue with prehybridization solutions containing ficoll, bovine serum albumin (BSA), polyvinyl pyrrolidone, and nucleic acids. Such blocking steps are time-consuming and expensive. As discussed below, the methods and compositions of the invention advantageously reduce and/or eliminate the need for such blocking steps and blocking reagents. However, in one embodiment, repetitive sequences may be suppressed according to the methods known in the art, e.g., as disclosed in PCT/US02/30573.

Bound probes may be detected in cytological and histological samples either directly or indirectly with fluorochromes (e.g., FISH), organic chromogens (e.g., CISH), silver particles (e.g., SISH), or other metallic particles (e.g., gold-facilitated fluorescence in situ hybridization, GOLDFISH). Thus, depending on the method of detection, populations of cells obtained from a sample to be tested may be visualized via fluorescence microscopy or conventional brightfield light microscopy.

Hybridization assays on cytological and histological samples are important tools for determining the number, size, and/or location of specific DNA sequences. For example, in CGH, whole genomes are stained and compared to normal reference genomes for the detection of regions with aberrant copy number. Typically, DNA from subject tissue and from normal control tissue is labeled with different colored probes. The pools of DNA are mixed and added to a metaphase spread of normal chromosomes (or to a microarray chip, for array- or matrix-CGH). The ratios of colors are then compared to identify regions with aberrant copy number.

FISH is typically used when multiple color imaging is required and/or when the protocol calls for quantification of signals. The technique generally entails preparing a cytological sample, labeling probes, denaturing target chromosomes and the probe, hybridizing the probe to the target sequence, and detecting the signal. Typically, the hybridization reaction fluorescently stains the targeted sequences so that their location, size, or number can be determined using fluorescence microscopy, flow cytometry, or other suitable instrumentation. DNA sequences ranging from whole genomes down to several kilobases can be studied using FISH. With enhanced fluorescence microscope techniques, such as, for example, deconvolution, even a single mRNA molecule can be detected. FISH may also be used on metaphase spreads and interphase nuclei.

FISH has been used successfully for mapping repetitive and single-copy DNA sequences on metaphase chromosomes, interphase nuclei, chromatin fibers, and naked DNA molecules, and for chromosome identification and karyotype analysis through the localization of large repeated families, typically the ribosomal DNAs and major tandem array families. One of the most important applications for FISH has been in detecting single-copy DNA sequences, in particular disease related genes in humans and other eukaryotic model species, and the detection of infections agents. FISH may be used to detect, e.g., chromosomal aneuploidy in prenatal diagnoses, hematological cancers, and solid tumors; gene abnormalities such as oncogene amplifications, gene deletions, or gene fusions; chromosomal structural abnormalities such as translocations, duplications, insertions, or inversions; contiguous gene syndromes such as microdeletion syndrome; the genetic effects of various therapies; viral nucleic acids in somatic cells and viral integration sites in chromosomes; etc. In multi-color FISH, each chromosome is stained with a separate color, enabling one to determine the normal chromosomes from which abnormal chromosomes are derived. Such techniques include multiplex FISH (m-FISH), spectral karyotyping (SKY), combined binary ration labeling (CO-BRA), color-changing karyotyping, cross-species color banding, high resolution multicolor banding, telomeric multiplex FISH (TM-FISH), split-signal FISH (ssFISH), and fusion-signal FISH.

CISH and SISH may be used for many of the same applications as FISH, and have the additional advantage of allowing for analysis of the underlying tissue morphology, for example in histopathology applications. If FISH is performed, the hybridization mixture may contain sets of distinct and balanced pairs of probes, as described in U.S. Pat. No. 6,730,474, which is incorporated herein by reference. For CISH, the hybridization mixture may contain at least one set of probes configured for detection with one or more conventional organic chromogens, and for SISH, the hybridization mixture may contain at least one set of probes configured for detection with silver particles, as described in Powell R D et al., "Metallographic in situ hybridization," Hum. Pathol., 38:1145-59 (2007).

The compositions of the invention may also be used fully or partly in all types of molecular biology techniques involving hybridization, including blotting and probing (e.g., Southern, northern, etc.), and arrays.

(3) Conditions for Performing Hybridization Assays

The method of the present invention involves the use of polar aprotic solvents in a stringent wash buffer for hybridization applications. The compositions of the present invention are particularly useful in said method.

A great variation exists in the traditional hybridization protocols known in the art. The stringent wash compositions of the invention may be used in any of the traditional hybridization protocols known in the art. For example, the heat pre-treatment, digestion, denaturation, hybridization, washes, and mounting steps may use the same conditions in terms of volumes, temperatures, reagents (aside from the stringent wash buffer), and incubation times as for traditional hybridization applications.

For example, in some embodiments, the denaturation temperature may vary from 60 to 100° C. and the hybridization temperature may vary from 20 to 60° C. In other embodiments, the denaturation temperature may vary from 60 to 70° C., 70 to 80° C., 80 to 90° C. or 90 to 100° C., and the hybridization temperature may vary from 20 to 30° C., 30 to 40° C., 40 to 50° C., or 50 to 60° C. In other embodiments, the denaturation temperature is 72, 82, or 92° C., and the hybridization temperature is 37, 40, 45, or 50° C.

In other embodiments, the denaturation time may vary from 0 to 10 minutes and the hybridization time may vary from 0 minutes to 24 hours. In other embodiments, the denaturation time may be from 0 to 5 minutes and the hybridization time may be from 0 minute to 8 hours. In other embodiments, the denaturation time is 0, 1, 2, 3, 4, or 5 minutes, and the hybridization time is 0 minutes, 5 minutes, 15 minutes, 30 minutes, 60 minutes, 180 minutes, or 240 minutes. It will be understood by those skilled in the art that in some cases, e.g., RNA detection, a denaturation step is not required.

Alternatively, assays using the compositions of the invention can be changed and optimized from traditional methodologies, for example, by decreasing the stringent wash time and/or decreasing the stringent wash temperatures.

After complementary strands of nucleic acid have reannealed in a hybridization application, the hybridization product will generally comprise complementary base pairing and non-complementary base pairing between the probe and the target nucleic acid. Any non-complementary base pairing is then removed by a series of post-hybridization washes. Four variables are typically adjusted to influence the stringency of the post-hybridization washes:

1. Temperature (as temperature increases, non-perfect matches between the probe and the target sequence will denature, i.e., separate, before more perfectly matched sequences).
2. Salt conditions (as salt concentration decreases, non-perfect matches between the probe and the target sequence will denature, i.e., separate, before more perfectly matched sequences).
3. Formamide concentration (as the amount of formamide increases, non-perfect matches between the probe and the target sequence will denature, i.e., separate, before more perfectly matched sequences).
4. Time (as the wash time increases, non-perfect matches between the probe and the target sequence will denature, i.e., separate, before more perfectly matched sequences).

Stringent wash methods using the compositions of the invention may involve applying the compositions to a hybridization product comprising a target nucleic acid sequence hybridized to a probe. During the stringent wash step, the polar aprotic solvent interacts with the hybridization product and facilitates the denaturation of the mismatched (i.e., non-complementary) sequences. The polar aprotic solvents specified in the present invention speed up this process, reduce the temperature required for the stringency wash, and reduce the harshness and toxicity of the stringency wash conditions compared to formamide-containing buffers.

Those skilled in the art will understand that different type of hybridization assays, different types of samples, different types of probe targets, different length of probes, different types of probes, e.g. DNA/RNA/PNA/LNA oligos, short DNA/RNA probes (0.5-3 kb), chromosome paint probes, CGH, repetitive probes (e.g. alpha-satellite repeats), single-locus etc., will effect the concentrations of e.g. salt and polar aprotic solvents required to obtain the most effective post-hybridization washes. The temperature and incubation time are also important variables for stringent washes using the compositions of the invention. In view of the guidance provided herein, one skilled in the art will understand how to vary these factors to optimize the stringency washes in hybridization applications.

The concentration of probe may be varied in order to produce strong signals and/or reduce background. For example, reducing probe concentration reduces background. However, reducing the probe concentration is inversely related to the hybridization time, i.e., the lower the concentration, the higher hybridization time required. Background levels can also be reduced by adding agents that reduce non-specific binding, such as to the cell membrane, such as small amounts of total human DNA or non-human-origin DNA (e.g., salmon sperm DNA) to a hybridization reaction using the compositions of the invention. However, the compositions of the invention often allow for better signal-to-noise ratios than traditional stringent assay wash compositions.

Traditional assay methods may also be changed and optimized when using the compositions of the invention depending on whether the system is manual, semi-automated, or fully automated. For example, a semi-automated or fully automated system will benefit from the lower temperature and shorter stringency washes obtained with the compositions of the invention. These features may reduce the difficulties encountered when traditional compositions are used in such systems. For example, one problem with semi-automated and fully automated systems is that significant evaporation of the sample can occur during the stringent wash step, since such systems require small sample volumes (e.g., 150 µL) and elevated temperatures. Thus, proportions of the components in traditional hybridization compositions are fairly invariable. However, since the compositions of the invention allow for stringent washes at lower temperatures, evaporation is reduced, allowing for increased flexibility in the proportions of the components in hybridization compositions used in semi-automated and fully automated systems.

Thus, the compositions and methods of the invention solve many of the problems associated with traditional hybridization compositions and methods.

The disclosure may be understood more clearly with the aid of the non-limiting examples that follow, which constitute preferred embodiments of the compositions according to the disclosure. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements. The examples that follow illustrate the present invention and should not in any way be considered as limiting the invention.

EXAMPLES

Reference will now be made in detail to specific embodiments of the invention. While the invention will be described in conjunction with these embodiments, it will be understood that they are not intended to limit the invention to those embodiments. On the contrary, the invention is intended to cover alternatives, modifications, and equivalents, which may be included within the invention as defined by the appended claims.

The reagents used in the following examples are from Dako's Histology FISH Accessory Kit (K5599) and Cytology FISH Accessory Kit (K5499) (Dako Denmark A/S, Glostrup Denmark). The kits contain all the key reagents, except for probe, required to complete a FISH procedure for formalin-fixed, paraffin-embedded tissue section specimens. All samples were prepared according to the manufacturer's description. The Dako Hybridizer (S2451, Dako) was used for the digestion, denaturation, and hybridization steps.

Evaluation of FISH slides was performed within a week after hybridization using a Leica DM6000B fluorescence microscope, equipped with DAPI, FITC, TEXAS RED single filters and FITC/TEXAS RED double filter under 10×, 20×, 40×, and 100× oil objective.

Evaluation of CISH slides was performed using an Olympus BX51 light microscope, under 4×, 10×, 20×, 40×, and 60× objective.

In the Examples that follow, "dextran sulfate" refers to the sodium salt of dextran sulfate (D8906, Sigma) having a molecular weight $M_w$>500,000. All concentrations of polar aprotic solvents are provided as v/v percentages. Phosphate buffer refers to a phosphate buffered solution containing $NaH_2PO_4$, $2H_2O$ (sodium phosphate dibasic dihydrate) and $Na_2HPO_4$, $H_2O$ (sodium phosphate monobasic monohydrate). Citrate buffer refers to a citrate buffered solution containing sodium citrate ($Na_3C_6H_5O_7$, $2H_2O$; 1.06448, Merck) and citric acid monohydrate ($C_6H_8O_7$, $H_2O$; 1.00244, Merck).

General Histology FISH/CISH Procedure for Examples 1-20

The slides with cut formalin-fixed paraffin embedded (FFPE) multiple tissue array sections from humans (tonsils, mammacarcinoma, kidney and colon) were baked at 60° C. for 30-60 min, deparaffinated in xylene baths, rehydrated in ethanol baths and then transferred to Wash Buffer. The samples were then pre-treated in Pre-Treatment Solution at a minimum of 95° C. for 10 min and washed 2×3 min. The samples were then digested with Pepsin RTU at 37° C. for 3 min, washed 2×3 min, dehydrated in a series of ethanol evaporations, and air-dried. The samples were then incubated with 10 µL FISH probe as described under the individual experiments. The samples were then washed by Stringency Wash at 65° C. 10 min, then washed 2×3 min, then dehydrated in a series of ethanol evaporations, and air-dried. Finally, the slides were mounted with 15 µL Antifade Mounting Medium. When the staining was completed, observers trained to assess signal intensity, morphology, and background of the stained slides performed the scoring.

General Cytology FISH Procedure for Examples 21 and 22

Slides with metaphases preparation were fixed in 3.7% formaldehyde for 2 min, washed 2×5 min, dehydrated in a series of ethanol evaporations, and air-dried. The samples were then incubated with 10 µL FISH probe as described under the individual experiments. The samples were then washed by Stringency Wash at 65° C. 10 min, then washed 2×3 min, then dehydrated in a series of ethanol evaporations, and air-dried. Finally, the slides were mounted with 15 μL Antifade Mounting Medium. When the staining was completed, observers trained to assess signal intensity and background of the stained slides performed the scoring as described in the scoring for guidelines for tissue sections.

General Histology FISH/CISH Procedure for Examples 23-26

Slides with cut formalin-fixed paraffin embedded (FFPE) multiple tissue array sections from humans (tonsils, mammacarcinoma, kidney and colon) were baked at 60° C. for 30-60 min, deparaffinated in xylene baths, rehydrated in ethanol baths and then transferred to Wash Buffer. The samples were then pre-treated in Pre-Treatment Solution at a minimum of 95° C. for 10 min and washed 2×3 min. The samples were then digested with Pepsin RTU at 37° C. for 3 min, washed 2×3 min, dehydrated in a series of ethanol evaporations, and air-dried. The samples were then incubated with 10 μL FISH probe denatured at 82° C. for 5 min and hybridized at 45° C. as described under the individual experiments. The samples were then washed as described under the individual experiments, dehydrated in a series of ethanol evaporations, and air-dried. Finally, the slides were mounted with 15 μL Antifade Mounting Medium. When the staining was completed, observers trained to assess signal intensity, morphology, and background of the stained slides performed the scoring.

Scoring Guidelines of Tissue Sections

The signal intensities were evaluated on a 0-3 scale with 0 meaning no signal and 3 equating to a strong signal. The cell/tissue structures are evaluated on a 0-3 scale with 0 meaning no structure and no nuclei boundaries and 3 equating to intact structure and clear nuclei boundaries. Between 0 and 3 there are additional grades 0.5 apart from which the observer can assess signal intensity, tissue structure, and background.

The signal intensity is scored after a graded system on a 0-3 scale.

| | |
|---|---|
| 0 | No signal is seen. |
| 1 | The signal intensity is weak. |
| 2 | The signal intensity is moderate. |
| 3 | The signal intensity is strong. |

The scoring system allows the use of ½ grades.

The tissue and nuclear structure is scored after a graded system on a 0-3 scale.

| | |
|---|---|
| 0 | The tissue structures and nuclear borders are completely destroyed. |
| 1 | The tissue structures and/or nuclear borders are poor. This grade includes situations where some areas have empty nuclei. |
| 2 | Tissue structures and/or nuclear borders are seen, but the nuclear borders are unclear. This grade includes situations where a few nuclei are empty. |
| 3 | Tissue structures and nuclear borders are intact and clear. |

The scoring system allows the use of ½ grades.

The background is scored after a graded system on a 0-3 scale.

| | |
|---|---|
| 0 | Little to no background is seen. |
| 1 | Some background. |
| 2 | Moderate background. |
| 3 | High Background. |

The scoring system allows the use of ½ grades.

Example 1

This example compares the signal intensity and cell morphology from samples treated with the compositions of the invention or traditional hybridization solutions as a function of denaturation temperature.

FISH Probe composition I: 10% dextran sulfate, 300 mM NaCl, 5 mM phosphate buffer, 40% formamide (15515-026, Invitrogen), 5 J.LM blocking PNAs (see Kirsten Vang Nielsen et al., *PNA Suppression Method Combined with Fluorescence In Situ Hybridisation (FISH) Technique inPRINS* and PNA Technologies in Chromosomal Investigation, Chapter 10 (Franck Pellestor ed.) (Nova Science Publishers, Inc. 2006)), 10 ng/μL TEXAS RED labeled CCND1 gene DNA probe (RP11-1143E20, size 192 kb).

FISH Probe composition II: 10% dextran sulfate, 300 mM NaCl, 5 mM phosphate buffer, 40% Ethylene carbonate (03519, Fluka), 5 μM blocking PNAs, 10 ng/μL Texas Red labeled CCND1 gene DNA probe (RP11-1143E20, size 192 kb).

Phases of different viscosity, if present, were mixed before use. The FISH probes were denatured as indicated for 5 min and hybridized at 45° C. for 60 minutes.

Results:

| | Signal | | Cell morphology | |
|---|---|---|---|---|
| Denaturation | (I) | (II) | | |
| temperature | Formamide | EC | Formamide | EC |
| 72° C. | 0 | 2 | Good | Good |
| 82° C. | ½ | 3 | Good | Good |
| 92° C. | ½ | 3 | Not good | Not good |

Signals scored as "3" were clearly visible in a 20× objective.

Example 2

This example compares the signal intensity and background staining from samples treated with the compositions of the invention or traditional hybridization solutions as a function of hybridization time.

FISH Probe composition I: 10% dextran sulfate, 300 mM NaCl, 5 mM phosphate buffer, 40% formamide, 5 μM blocking PNAs, 10 ng/μL TEXAS RED labeled CCND1 gene DNA probe.

FISH Probe composition II: 10% dextran sulfate, 300 mM NaCl, 5 mM phosphate buffer, 40% Ethylene carbonate, 5 μM blocking PNAs, 10 ng/μL TEXAS RED labeled CCND1 gene DNA probe.

Phases of different viscosity, if present, were mixed before use. The FISH probes were incubated at 82° C. for 5 min and then at 45° C. for 14 hours, 4 hours, 2 hours, 60 minutes, 30 minutes, 15 minutes, 0 minutes.

Results:

| | Signal | | Background staining | |
|---|---|---|---|---|
| Hybridization | (I) | (II) | | |
| time | Formamide | EC | Formamide | EC |
| 14 hours | 3 | 3 | +½ | +2 |
| 4 hours | 1 | 3 | +½ | +1 |
| 2 hours | ½ | 3 | +0 | +1 |
| 60 min. | ½ | 3 | +0 | +1 |

-continued

| Hybridization | Signal | | Background staining | |
|---|---|---|---|---|
| time | (I) Formamide | (II) EC | Formamide | EC |
| 30 min. | 0 | 2½ | +0 | +1 |
| 15 min. | 0 | 2 | +0 | +1 |
| 0 min. | 0 | 1 | +0 | +½ |

Signals scored as "3" were clearly visible in a 20x objective.

Example 3

This example compares the signal intensity from samples treated with the compositions of the invention having different polar aprotic solvents or traditional hybridization solutions.

FISH Probe composition I: 10% dextran sulfate, 300 mM NaCl, 5 mM phosphate buffer, 40% formamide, 5 µM blocking PNAs, 10 ng/µL TEXAS RED labeled CCND1 gene DNA probe.

FISH Probe composition II: 10% dextran sulfate, 300 mM NaCl, 5 mM phosphate buffer, 40% Ethylene carbonate (EC), 5 µM blocking PNAs, 10 ng/µL TEXAS RED labeled CCND1 gene DNA probe.

FISH Probe composition III: 10% dextran sulfate, 300 mM NaCl, 5 mM phosphate buffer, 40% Propylene carbonate (PC) (540013, Aldrich), 5 µM blocking PNAs, 10 ng/µL TEXAS RED labeled CCND1 gene DNA probe.

FISH Probe composition IV: 10% dextran sulfate, 300 mM NaCl, 5 mM phosphate buffer, 40% Sulfolane (SL) (T22209, Aldrich), 5 µM blocking PNAs, 10 ng/µL TEXAS RED labeled CCND1 gene DNA probe.

FISH Probe composition V: 10% dextran sulfate, 300 mM NaCl, 5 mM phosphate buffer, 40% Aceto nitrile (AN) (C02CIIX, Lab-Scan), 5 µM blocking PNAs, 10 ng/µL TEXAS RED labeled CCND1 gene DNA probe.

FISH Probe composition VI: 10% dextran sulfate, 300 mM NaCl, 5 mM phosphate buffer, 40% γ-butyrolactone (GBL) (B103608, Aldrich), 5 µM blocking PNAs, 7.5 ng/µL TEXAS RED labeled CCNDl gene DNA probe.

Phases of different viscosity, if present, were mixed before use. The FISH probes were incubated at 82° C. for 5 min and then at 45° C. for 60 minutes.
Results:

| Signal | | | | | |
|---|---|---|---|---|---|
| (I) Formamide | (II) EC | (III) PC | (IV) SL | (V) AN | (VI) GBL |
| ½ | 3 | 3 | 3 | 2 | 3 |

Signals scored as "3" were clearly visible in a 20x objective.

Example 4

This example compares the signal intensity from samples treated with the compositions of the invention having different concentrations of polar aprotic solvent.

FISH Probe Compositions: 10% dextran sulfate, 300 mM NaCl, 5 mM phosphate buffer, 10-60% Ethylene carbonate (as indicated), 5 µM blocking PNAs, 7.5 ng/µL TEXAS RED labeled IGK-constant DNA gene probe ((CTD-3050EI5, RP11-1083E8; size 227 kb) and 7.5 ng/µL FITC labeled IGK-variable gene DNA probe (CTD-2575M21, RP11-122B6, RP11-316G9; size 350 and 429 kb).

Phases of different viscosity, if present, were mixed before use. The FISH probes were incubated at 82° C. for 5 min and then at 45° C. for 60 minutes.
Results:

| | | Ethylene Carbonate (EC) | | | | |
|---|---|---|---|---|---|---|
| | | 10% | 20% | 30% | 40% | 60% |
| Signal Intensity | TEXAS RED | 1½ | 2 | 3 | 3 | 2 |
| | FITC | 1 | 1½ | 2 | 2½ | 2 |

Signals scored as "3" were clearly visible in a 20x objective.

Example 5

This example compares the signal intensity and background intensity from samples treated with the compositions with and without PNA blocking.

FISH Probe Compositions: 10% dextran sulfate, 300 mM NaCl, 5 mM phosphate buffer, 40% Ethylene carbonate, 7.5 ng/µL TEXAS RED labeled CCND1 gene DNA probe.

Phases of different viscosity, if present, were mixed before use. The FISH probes were incubated at 82° C. for 5 min and then at 45° C. for 60 minutes.
Results:

| | Ethylene carbonate (EC) | |
|---|---|---|
| | PNA-blocking | Non-PNA blocking |
| Signal intensity | 3 | 3 |
| Background intensity | ½+ | ½+ |

Signals scored as "3" were clearly visible in a 20x objective.

Example 6

This example compares the signal intensity from samples treated with the compositions of the invention as a function of probe concentration and hybridization time.

FISH Probe Compositions: 10% dextran sulfate, 300 mM NaCl, 5 mM phosphate buffer, 40% Ethylene carbonate, and 10, 7.5, 5 or 2.5 ng/µL TEXAS RED labeled CCND1 gene DNA probe (as indicated).

Phases of different viscosity, if present, were mixed before use. The FISH probes were incubated at 82° C. for 5 min and then at 45° C. for 3 hours, 2 hours and 1 hours.
Results:

| | Signal Intensity | | | |
|---|---|---|---|---|
| Hybridization time | (I) 10 ng/µL | (II) 7.5 ng/µL | (III) 5 ng/µL | (IV) 2.5 ng/µL |
| 3 hours | 3 | 3 | 3 | 3 |
| 2 hours | 3 | 3 | 3 | 1 |
| 1 hours | 3 | 3 | 3 | ½ |

Signals scored as "3" were clearly visible in a 20x objective.

Example 7

This example compares the signal intensity from samples treated with the compositions of the invention as a function of salt, phosphate, and buffer concentrations.

FISH Probe Compositions: 10% dextran sulfate, ([NaCl], [phosphate buffer], [TRIS buffer] as indicated in Results), 40% Ethylene carbonate, 7.5 ng/μL TEXAS RED labeled CCNDI gene DNA probe.

Phases of different viscosity, if present, were mixed before use. The FISH probes were incubated at 82° C. for 5 min and then at 45° C. for 60 minutes.

Results:

|  | [NaCl] | | |
| --- | --- | --- | --- |
|  | 300 mM | 100 mM | 0 mM |
| Signal intensity phosphate [0 mM] | 2 | 1 | ½ |
| Signal intensity phosphate [5 mM] | 3 | 2½ | ½ |
| Signal intensity phosphate [35 mM] | — | — | 3 |
| Signal intensity TRIS [40 mM] | — | — | 2 |

Signals scored as "3" were clearly visible in a 20x objective.

Example 8

This example compares the signal intensity from samples treated with the compositions of the invention as a function of dextran sulfate concentration.

FISH Probe Compositions: 0, 1, 2, 5, or 10% dextran sulfate (as indicated), 300 mM NaCl, 5 mM phosphate buffer, 40% Ethylene carbonate, 5 ng/μL TEXAS RED labeled SIL-TAL1 gene DNA probe (RPI-278013; size 67 kb) and 6 ng/μL FITC SIL-TAL1 (ICRFc112-112C1794, RP11-184J23, RP11-8J9, CTD-2007B18, 133B9; size 560 kb).

Phases of different viscosity, if present, were mixed before use. The FISH probes were incubated at 81° C. for 5 min and then at 45° C. for 60 minutes. No blocking.

Results:

|  | Signal Intensity | |
| --- | --- | --- |
| % Dextran Sulfate | TEXAS RED Probe | FITC Probe |
| 0% | 1 | 1 |
| 1% | 1 | 1 |
| 2% | 1 | 1½ |
| 5% | 2 | 2½ |
| 10% | 2 | 2½ |

NOTE:
this experiment did not produce results scored as "3" because the SIL-TAL1 TEXAS RED labeled probe is only 67 kb and was from a non-optimized preparation.

TEXAS RED labeled probe is only 67 kb and was from a non-optimized preparation.

Example 9

This example compares the signal intensity from samples treated with the compositions of the invention as a function of dextran sulfate, salt, phosphate, and polar aprotic solvent concentrations.

FISH Probe Composition Ia: 34% dextran sulfate, 0 mM NaCl, 0 mM phosphate buffer, 0% ethylene carbonate, 10 ng/μL TEXAS RED labeled HER2 gene DNA probe (size 218 kb) and 50 nM of FITC-labeled CEN-7 PNA probe.

FISH Probe Composition Ib: 34% dextran sulfate, 300 mM NaCl, 5 mM phosphate buffer, 0% ethylene carbonate, 10 ng/μL TEXAS RED labeled HER2 gene DNA probe (size 218 kb) and 50 nM of FITC-labeled CEN-7 PNA probe.

FISH Probe Composition Ic: 34% dextran sulfate, 600 mM NaCl, 10 mM phosphate buffer, 0% ethylene carbonate, 10 ng/μL TEXAS RED labeled HER2 gene DNA probe (size 218 kb) and 50 nM of FITC-labeled CEN-7 PNA probe.

FISH Probe Composition IIa: 32% dextran sulfate, 0 mM NaCl, 0 mM phosphate buffer, 5% ethylene carbonate, 10 ng/μL TEXAS RED labeled HER2 gene DNA probe (size 218 kb) and 50 nM of FITC-labeled CEN-7 PNA probe.

FISH Probe Composition IIb: 32% dextran sulfate, 300 mM NaCl, 5 mM phosphate buffer, 5% ethylene carbonate, 10 ng/μL TEXAS RED labeled HER2 gene DNA probe (size 218 kb) and 50 nM of FITC-labeled CEN-7 PNA probe.

FISH Probe Composition IIc: 32% dextran sulfate, 600 mM NaCl, 10 mM phosphate buffer, 5% ethylene carbonate, 10 ng/μL TEXAS RED labeled HER2 gene DNA probe (size 218 kb) and 50 nM of FITC-labeled CEN-7 PNA probe.

FISH Probe Composition IIIa: 30% dextran sulfate, 0 mM NaCl, 0 mM phosphate buffer, 10% ethylene carbonate, 10 ng/μL TEXAS RED labeled HER2 gene DNA probe (size 218 kb) and 50 nM of FITC-labeled CEN-7 PNA probe.

FISH Probe Composition IIIb: 30% dextran sulfate, 300 mM NaCl, 5 mM phosphate buffer, 10% ethylene carbonate, 10 ng/μL TEXAS RED labeled HER2 gene DNA probe (size 218 kb) and 50 nM of FITC-labeled CEN-7 PNA probe.

FISH Probe Composition IIIc: 30% dextran sulfate, 600 mM NaCl, 10 mM phosphate buffer, 10% ethylene carbonate, 10 ng/μL TEXAS RED labeled HER2 gene DNA probe (size 218 kb) and 50 nM of FITC-labeled CEN-7 PNA probe.

FISH Probe Composition IVa: 28% dextran sulfate, 0 mM NaCl, 0 mM phosphate buffer, 15% ethylene carbonate, 10 ng/μL TEXAS RED labeled HER2 gene DNA probe (size 218 kb) and 50 nM of FITC-labeled CEN-7 PNA probe.

FISH Probe Composition IVb: 28% dextran sulfate, 300 mM NaCl, 5 mM phosphate buffer, 15% ethylene carbonate, 10 ng/μL TEXAS RED labeled HER2 gene DNA probe (size 218 kb) and 50 nM of FITC-labeled CEN-7 PNA probe.

FISH Probe Composition IVc: 28% dextran sulfate, 600 mM NaCl, 10 mM phosphate buffer, 15% ethylene carbonate, 10 ng/μL TEXAS RED labeled HER2 gene DNA probe (size 218 kb) and 50 nM of FITC-labeled CEN-7 PNA probe.

FISH Probe Reference V: Standard sales vial of HER2 PharmDx probe mix (K5331, Dako) containing blocking PNA. Overnight hybridization for 20 hours.

All compositions were present as a single phase. The FISH probes were incubated at 82° C. for 5 min and then at 45° C. for 60 minutes with no blocking, except for FISH Probe Reference V, which had PNA blocking and was hybridized for 20 hours.

Results:

|  | Signal Strength | |
| --- | --- | --- |
|  | DNA Probes | PNA Probes |
| Composition Ia | 0 | ½ |
| Composition Ib | 0 | ½ |
| Composition Ic | ½ | 2½ |
| Composition IIa | ½ | 3 |
| Composition IIb | 1 | 2 |
| Composition IIc | ½ | 3 |
| Composition IIIa | 1 | 2½ |
| Composition IIIb | 1½ | 2½ |
| Composition IIIc | 2 | 3 |
| Composition IVa | 2½-3 | 3 |
| Composition IVb | 3 | 3 |

-continued

| | Signal Strength | |
| --- | --- | --- |
| | DNA Probes | PNA Probes |
| Composition IVc | 3 | 3 |
| Reference V | 2 | 2½ |

NOTE:
Composition IVa gave strong DNA signals with no salt. This is not possible with standard FISH compositions, where DNA binding is salt dependent.

Example 10

This example compares the signal intensity from samples treated with the compositions of the invention as a function of polar aprotic solvent and dextran sulfate concentration under high salt (4× normal) conditions.

FISH Probe Composition I: 0% ethylene carbonate, 29% dextran sulfate, 1200 mM NaCl, 20 mM phosphate buffer, 10 ng/µL TEXAS RED labeled HER2 gene DNA probe and 50 nM of FITC-labeled CEN-7 PNA probe. Composition was a single phase.

FISH Probe Composition II: 5% ethylene carbonate, 27% dextran sulfate, 1200 mM NaCl, 20 mM phosphate buffer, 10 ng/µL TEXAS RED labeled HER2 gene DNA probe and 50 nM of FITC-labeled CEN-7 PNA probe. Composition was a single phase.

FISH Probe Composition III: 10% ethylene carbonate, 25% dextran sulfate, 1200 mM NaCl, 20 mM phosphate buffer, 10 ng/µL TEXAS RED labeled HER2 gene DNA probe and 50 nM of FITC-labeled CEN-7 PNA probe. Composition was a single phase.

FISH Probe Composition IV (not tested): 20% ethylene carbonate, 21% dextran sulfate, 1200 mM NaCl, 20 mM phosphate buffer, 10 ng/µL TEXAS RED labeled HER2 gene DNA probe and 50 nM of FITC-labeled CEN-7 PNA probe. Composition had two phases.

Results:

| | Signal Strength | |
| --- | --- | --- |
| | DNA Probes | PNA Probes |
| Composition I | ½ | 3 |
| Composition II | 2 | 2½ |
| Composition III | 3 | 3 |
| Composition IV | — | — |

Note:
Composition II gave good DNA signals with only 5% EC and strong DNA signals with 10% EC.

Example 11

This example compares the signal intensity and background from samples treated with different phases of the compositions of the invention.

FISH Probe Composition: 10% dextran sulfate, 300 mM NaCl, 5 mM phosphate buffer, 40% Ethylene carbonate, 8 ng/µL TEXAS RED labeled HER2 gene DNA probe and 600 nM FITC-labeled CEN-17 PNA probe. The FISH probes were incubated at 82° C. for 5 min and then at 45° C. for 60 minutes. No blocking.

Results:

| | Signal Intensity | | |
| --- | --- | --- | --- |
| | DNA Probe | PNA Probe | Background |
| Upper Phase | 3 | 1½ | +2 |
| Lower Phase | 3 | 2½ | +1 |
| Mix of Upper and Lower Phases | 2½ | 3 | +½ |

NOTE:
the upper phase had more background than the lower phase in these experiments.

Example 12

This example is similar to the previous example, but uses a different DNA probe and GBL instead of EC.

FISH Probe Composition: 10% dextran sulfate, 300 mM NaCl, 5 mM phosphate buffer, 40% GBL, 10 ng/µL TEXAS RED labeled CCND1 gene DNA probe and 600 nM FITC-labeled CEN-17 PNA probe.

The FISH probes were incubated at 82° C. for 5 min and then at 45° C. for 60 minutes. No blocking.

Results:

| | Signal Strength | | |
| --- | --- | --- | --- |
| | DNA Probe | PNA Probe | Background |
| Top Phase | 3 | 0-½ | +1½ |
| Bottom Phase | 2 | ½ | +3 |
| Mixed Phases | 2½ | ½ | +2½ |

Example 13

This example examines the number of phases in the compositions of the invention as a function of polar aprotic solvent and dextran sulfate concentration.

FISH Probe Compositions: 10 or 20% dextran sulfate; 300 mM NaCl; 5 mM phosphate buffer; 0, 5, 10, 15, 20, 25, 30% EC; 10 ng/µL probe.

Results:

| % EC | Number of Phases 10% Dextran | Number of Phases 20% Dextran |
| --- | --- | --- |
| 0 | 1 | 1 |
| 5 | 1 | 1 |
| 10 | 1 | 1 |
| 15 | 1 | 1 |
| 20 | 2 | 2 |
| 25 | 2 | 2 |
| 30 | 2 | 2 |

NOTE:
15% EC, 20% dextran sulfate produces the nicest high signal intensities of the above one phase solution. Two phases 20% EC has even higher signal intensities than 15%. (Data not shown).

Example 14

This example compares the signal intensity and background from samples treated with different compositions of the invention as a function of probe concentration and hybridization time.

FISH Probe Composition I: 10 ng/µL HER2 TxRed labeled DNA probe (standard concentration) and standard concentration of CEN7 FITC labeled PNA probe (50 nM); 15% EC; 20% dextran sulfate; 600 mM NaCl; 10 mM phosphate buffer.

FISH Probe Composition II: 5 ng/μL HER2 TxRed labeled DNA probe (½ of standard concentration) and standard concentration (50 nM) of FITC labeled CEN7 PNA probes; 15% EC; 20% dextran sulfate; 600 mM NaCl; 10 mM phosphate buffer.

FISH Probe Composition III: 2.5 ng/μL HER2 TxRed labeled DNA probe (¼ of standard concentration) and ½ of the standard concentration (25 nM) of CEN7 PNA probes; 15% EC; 20% dextran sulfate; 600 mM NaCl; 10 mM phosphate buffer.

Compositions I-III existed as a single phase. The FISH probes were incubated at 82° C. for 5 min and then at 45° C. for 3 hours, 2 hours and 1 hours.

Results:

| Hybrid-ization time | Signal Intensity | | | | | | | | |
|---|---|---|---|---|---|---|---|---|---|
| | I | | | II | | | III | | |
| | DNA | PNA | B.G. | DNA | PNA | B.G. | DNA | PNA | B.G. |
| 3 hours | 3 | 3 | +3 | 3 | 3 | +2.5 | 3 | 3 | +1.5 |
| 2 hours | 2.5 | 2.5 | +3 | 3 | 3 | +3 | 3 | 3 | +1.5 |
| 1 hours | 2.5 | 2.5 | +3 | 3 | 3 | +1.5 | 2.5 | 3 | +1 |

Signals scored as "3" were clearly visible in a 20x objective. B.G.: Back ground.

Example 15

This example compares the signal intensity and background from samples treated with the compositions of the invention as a function of blocking agent.

FISH Probe Compositions: 15% EC; 20% dextran sulfate; 600 mM NaCl; 10 mM phosphate buffer; 2.5 ng/μL HER2 TxRed labeled DNA probe (¼ of standard concentration) and ½ of the standard concentration (300 nM) FITC labeled CEN17 PNA probe. Samples were blocked with: (a) nothing; (b) 0.1 μg/μL COT1 (15279-011, Invitrogen); (c) 0.3 μg/μL COT1; or (d) 0.1 μg/μL total human DNA before hybridization using the compositions of the invention.

All samples were present as a single phase. The FISH probes were incubated at 82° C. for 5 min and then at 45° C. for 60 minutes.

Results:

| | Signal Intensity | | |
|---|---|---|---|
| Blocking Agent | Background | DNA | PNA |
| Nothing | +1-1.5 | 3 | 2.5 |
| 0.1 μg/μL COT1 | +1 | 3 | 2.5 |
| 0.3 μg/μL COT1 | +1.5 | 3 | 2.5 |
| 0.1 μg/μL total human DNA | +½ | 3 | 2.5 |

NOTE:
Background levels without blocking are significantly lower than what is normally observed by standard FISH with no blocking. In contrast, if a standard FISH composition does not contain a blocking agent, signals normally cannot be read.

Example 16

This experiment compares different ways of removing background staining using the compositions of the invention.

All compositions contained 15% EC, 20% dextran sulfate, 600 mM NaCl, 10 mM phosphate buffer, 2.5 ng/μL HER2 DNA probes (¼ of standard concentration), 300 nM CEN17 PNA probe (½ of standard concentration), and one of the following background-reducing agents:

A) 5 μM blocking-PNA (see Kirsten Vang Nielsen et al., *PNA Suppression Method Combined with Fluorescence In Situ Hybridisation (FISH) Technique* in PRINS and PNA Technologies in Chromosomal Investigation, Chapter 10 (Franck Pellestor ed.) (Nova Science Publishers, Inc. 2006))
B) 0.1 μg/μL COT-1 DNA
C) 0.1 μg/μL total human DNA (THD) (sonicated unlabelled THD)
D) 0.1 μg/μL sheared salmon sperm DNA (AM9680, Ambion)
E) 0.1 μg/μL calf thymus DNA (D8661, Sigma)
F) 0.1 μg/μL herring sperm DNA (D7290, Sigma)
G) 0.5% formamide
H) 2% formamide
I) 1% ethylene glycol (1.09621, Merck)
J) 1% glycerol (1.04095, Merck)
K) 1% 1,3-Propanediol (533734, Aldrich)
L) 1% $H_2O$ (control)

All samples were present as a single phase. The probes were incubated at 82° C. for 5 minutes and then at 45° C. on FFPE tissue sections for 60 and 120 minutes.

Results:

| | | | Signal Intensity | |
|---|---|---|---|---|
| Background blocking | Hybridization/min | Background | DNA | PNA |
| Blocking-PNA | 60 | +1 | 3 | 2.5 |
| Blocking-PNA | 120 | +1-1½ | 3 | 2.5 |
| COT-1 | 60 | +½ | 3 | 2.5 |
| COT-1 | 120 | +0-½ | 3 | 2.5 |
| THD | 60 | +0 | 3 | 3 |
| THD | 120 | +½ | 3 | 2.5 |
| Salmon DNA sperm | 60 | +0 | 3 | 3 |
| Salmon DNA sperm | 120 | +0 | 3 | 3 |
| Calf Thymus DNA | 60 | +0 | 2.5 | 3 |
| Calf Thymus DNA | 120 | +½ | 3 | 2.5 |
| Hearing sperm DNA | 60 | +0 | 3 | 3 |
| Hearing sperm DNA | 120 | +½ | 2.5 | 3 |
| 0.5% formamide | 60 | +0 | 2.5 | 3 |
| 0.5% formamide | 120 | +0 | 3 | 3 |
| 2% formamide | 60 | +½ | 2.5 | 3 |
| 2% formamide | 120 | +½ | 3 | 3 |
| 1% Ethylene Glycol | 60 | +½ | 2.5 | 3 |
| 1% Ethylene Glycol | 120 | +1½ | 3 | 2.5 |
| 1% Glycerol | 60 | +½ | 0.5 | 3 |
| 1% Glycerol | 120 | +1 | 3 | 2.5 |
| 1% 1,3-Propanediol | 60 | +0 | 3 | 2.5 |
| 1% 1,3-Propanediol | 120 | +1 | 3 | 2.5 |
| Nothing | 60 | +1 | 2.5 | 2.5 |
| Nothing | 120 | +1½ | 3 | 2.5 |

NOTE:
all background reducing reagents, except for blocking-PNA, showed an effect in background reduction. Thus, specific blocking against repetitive DNA sequences is not required.

Example 17

This experiment compares the signal intensity from the upper and lower phases using two different polar aprotic solvents.

FISH Probe Composition I: 10% dextran sulfate, 300 mM NaCl, 5 mM phosphate buffer, 40% ethylene trithiocarbonate (ET) (E27750, Aldrich), 5 μM blocking PNAs, 10 ng/μL TEXAS RED labeled CCND1 gene DNA probe.

FISH Probe Composition II: 10% dextran sulfate, 300 mM NaCl, 5 mM phosphate buffer, 40% glycol sulfite (GS) (G7208, Aldrich), 5 μM blocking PNAs, 10 ng/μL TEXAS RED labeled CCND1 gene DNA probe.

The FISH probes were incubated at 82° C. for 5 min and then at 45° C. for 60 minutes.

Results:

|  | Signal Intensity | |
| --- | --- | --- |
|  | I (ET) | II (GS) |
| Upper Phase | 1½ | 0 |
| Lower Phase | 0 | 3 |
| Mix of Upper and Lower Phases | 2½ | 3 |

Example 18

This experiment examines the ability of various polar aprotic solvents to form a one-phase system.

All compositions contained: 20% dextran sulfate, 600 mM NaCl, 10 mM phosphate buffer, and either 10, 15, 20, or 25% of one of the following polar aprotic solvents:
Sulfolane
γ-Butyrolactone
Ethylene trithiocarbonate
Glycol sulfite
Propylene carbonate Results: all of the polar aprotic solvents at all of the concentrations examined produced at least a two-phase system in the compositions used. However, this does not exclude that these compounds can produce a one-phase system under other composition conditions.

Example 19

This experiment examines the use of the compositions of the invention in chromogenic in situ hybridization (CISH) analysis on multi FFPE tissue sections.

FISH Probe Composition I: 4.5 ng/μL TCRAD FITC labelled gene DNA probe (¼ of standard concentration) (RP11-654A2, RP11-246A2, CTP-2355L21, RP11-158G6, RP11-780M2, RP11-481C14; size 1018 kb); 15% EC; 20% dextran sulfate; 600 mM NaCl; 10 mM citrate buffer, pH 6.0.

FISH Probe Composition II: 4.5 ng/μL TCRAD FITC labelled gene DNA probe (¼ of standard concentration) (size 1018 kb); 15% EC; 20% dextran sulfate; 600 mM NaCl; 10 mM citrate buffer, pH 6.0; 0.1 ug/uL sheared salmon DNA sperm.

FISH Probe Composition III: 300 nM of each individual FITC labelled PNA CEN17 probe (½ of standard concentration); 15% EC; 20% dextran sulfate; 600 mM NaCl; 10 mM citrate buffer, pH 6.0.

All samples were analyzed using the Dako DuoCISH protocol (SK108) and compositions for split probes with the exception that the stringency wash was conducted for 20 minutes instead of 10 minutes, and without using the DuoCISH red chromogen step.

Results:

|  | Signal Strength | |
| --- | --- | --- |
| Composition | FITC DNA | FITC PNA |
| I | 3 | — |
| II | 3 | — |
| III | — | 3 |

Note:
The signal intensities were very strong. Due to the high levels of background, it was not possible to discriminate if addition of salmon sperm DNA in Composition II reduced the background. Signals were clearly visible using a 10x objective in e.g. tonsils, which in general had less background. If tissues possessed high background, the signals were clearly visible using a 20x objective.

Example 20

This example compares the signal intensity and background from FFPE tissue sections treated with the compositions of the invention with two DNA probes.

FISH Probe Composition I: 9 ng/μL IGH FITC labelled gene DNA probe (RP11-151B17, RP11-112H5, RP11-101G24, RP11-12F16, RP11-47P23, CTP-3087C18; size 612 kb); 6.4 ng/μL MYC Tx Red labeled DNA probe (CTD-2106F24, CTD-2151C21, CTD-2267H22; size 418 kb); 15% EC; 20% dextran sulfate; 600 mM NaCl; 10 mM citrate buffer, pH 6.0.

FISH Probe Composition II: 9 ng/μL IGH FITC labelled gene DNA probe; 6.4 ng MYC TxRed labeled DNA probe; 15% EC, 20% dextran sulfate; 600 mM NaCl; 10 mM citrate buffer, pH 6.0; 0.1 ug/uL sheared salmon sperm DNA.

|  | Signal Strength | | |
| --- | --- | --- | --- |
| Salmon DNA | FITC probe | TEXAS RED probe | Background |
| − | 2½ | 2½ | +2.5 |
| + | 3 | 3 | +1.5 |

NOTE:
the high background was probably due to the fact that standard probe concentrations were used.

Example 21

This experiment examines the use of the compositions of the invention on cytological samples.

FISH Probe Composition: 15% EC; 20% dextran sulfate; 600 mM NaCl; 10 mM phosphate buffer; 5 ng/μL HER2 TxRed labeled DNA probe (½ of standard concentration) and ½ of the standard concentration of CEN7 (25 nM).

The FISH probes were incubated on metaphase chromosome spreads at 82° C. for 5 minutes, then at 45° C. for 30 minutes, all without blocking.

Results:

| Signal Strength | | |
| --- | --- | --- |
| DNA Probe | PNA Probe | Background |
| 3 | 3 | +1 |

No chromosome banding (R-banding pattern) was observed with the compositions of the invention, in contrast with traditional ISH solutions, which typically show R-banding. A low homogenously red background staining of the interphase nuclei and metaphase chromosomes was observed.

Example 22

This example compares the signal intensity and background from DNA probes on cytology samples, metaphase spreads, with and without blocking.

FISH Probe Composition I: 6 ng/μL TEXAS RED labelled gene DNA probe (standard concentration) (CTP-31666K20, CTP-2373N7; size 301 kb) and 4.5 ng/μL FITC labelled gene DNA probe (¼ of standard concentration); 15% EC, 20% dextran sulfate; 600 mM NaCl; 10 mM citrate buffer, pH 6.0.

FISH Probe Composition II: 6 ng/μL TCRAD TEXAS RED labelled gene DNA probe (standard concentration) (size 301 kb) and 4.5 ng/μL FITC labelled gene DNA probe (¼ of standard concentration); 15% EC, 20% dextran sulfate; 600 mM NaCl; 10 mM citrate buffer, pH 6.0; 0.1 ug/uL sheared salmon sperm DNA.

The FISH probes were incubated on metaphase spreads at 82° C. for 5 min, then at 45° C. for 60 min.
Results:

| Blocking Agent | Background | Signal Intensity | |
| --- | --- | --- | --- |
| | | TEXAS RED | FITC |
| Nothing | +0 | 3 | 3 |
| 0.1 µg/µL Salmon DNA | +0 | 3 | 3 |

Again, no chromosome banding (R-banding pattern) was observed with the compositions of the invention. In addition, no background staining of the interphase nuclei or the metaphase chromosomes were observed.

Example 23

This example compares the background and signal intensity as a function of the stringency wash conditions.

Stringency wash composition I: 2×SSC (pH 7.0)
Stringency wash composition II: 2×SSC (pH 7.0), 50% EC (E2, 625-8, Sigma-Aldrich)
Stringency wash composition III: 2×SSC (pH 7.0), 50% formamide (15515-026, Invitrogen)

FISH Probe Composition A: 2.5 ng/µL HER2 TxRed labeled DNA probe (¼ of standard concentration) and ½ of the standard concentration (300 nM) of CEN17 PNA probes; 15% EC, 20% dextran sulfate; 600 mM NaCl; 10 mM citrate buffer, pH 6.0.

FISH Probe Composition B: Standard sales vial of HER2PharmDx probe mix (K5331, Dako) containing blocking PNA and formamide.

Samples were denatured at 82° C. for 5 min., hybridized at 45° for 1 h for FISH Probe Composition A and overnight (20 hours) for FISH Probe Composition B. All stringency washes were performed at 42° C. for 15 min followed by a wash in 2×SCC at 42° C. for 3×5 min.
Results:

| Stringency Wash | Probe buffer | Background | Signal Intensity | |
| --- | --- | --- | --- | --- |
| | | | DNA | PNA |
| Reference (I) | EC (A) | +3.0 | 1.5 | 2.5 |
| EC (II) | EC (A) | +2 | 2.5 | 2.5 |
| Formamide (III) | EC (A) | +1½ | 2.5 | 2.5 |
| Reference (I) | Formamide (B) | +1 | 2.5 | 2.5 |
| EC (II) | Formamide (B) | +½ | 3 | 3 |
| Formamide (III) | Formamide (B) | +½ | 3 | 2.5 |

These results show that the buffers of the invention produce reduced background staining compared with 2×SSC wash buffer (Stringency wash composition I). These results also show that the buffers of the invention can be used instead of formamide-containing buffers for stringency washes at 42° C.

Example 24

This example compares the background and signal intensity as a function of the stringency wash conditions. The reference was done as described in the methods of the "general application".

This example used a standard sales vial of HER2PharmDx probe mix (K5331, Dako) containing 10 ng/µL HER2 TxRed labeled DNA probe and (600 nM) of CEN17 PNA probes, 45% formamide, 10% dextran sulfate, 300 mM NaCl, 5 mM Phosphate buffer, 5 µM unlabelled blocking PNAs.

Stringency wash composition I: 2×SSC (pH 7.0), 20% EC (E2, 625-8, Sigma-Aldrich)
Stringency wash composition 2×SSC (pH 7.0), 50% EC (E2, 625-8, Sigma-Aldrich)
Stringency wash composition III: 1× Stringency Buffer (vial 4, K5599, Dako)

The samples were denatured at 82° C. for 5 min. and hybridized overnight (20 hours). The stringency wash for compositions I and II was performed at 45° C. for 15 min. followed by a wash in 2×SCC at 45° C. for 3×5 min. The stringent wash for composition III was performed at 65° C. for 10 min. followed by a wash for 2×3 min. in Wash buffer (Vial 3, K5599).
Results:

| Stringency Wash | Temperature | Background | Signal Intensity | |
| --- | --- | --- | --- | --- |
| | | | DNA | PNA |
| 20% EC (I) | 45° C./15 min | +½ | 2½ | 2½ |
| 50% EC (II) | 45° C./15 min | +½ | 2½ | 2½ |
| Reference (III) | 65° C./10 min | +½ | 2½ | 2½ |

These results show that at 45° C., the buffers of the invention produce similar levels of background as traditional stringent wash buffers at 65° C. Thus, the buffers of the invention can be used to produce low background under low temperature stringency wash conditions.

Example 25

This example compares the background and signal intensity as a function of the stringency wash conditions.

This example used a standard sales vial of HER2PharmDx probe mix (K5331, Dako) containing 10 ng/µL HER2 TxRed labeled DNA probe and (600 nM) of CEN17 PNA probes, 45% formamide, 10% dextran sulfate, 300 mM NaCl, 5 mM Phosphate buffer, 5 µM unlabelled blocking PNAs.

Stringency wash composition I: 2×SSC (pH 7.0), 20% SL
Stringency wash composition II: 2×SSC (pH 7.0), 20% GBL
Stringency wash composition III: 1× Stringency Buffer vial 4, K5599, Dako)

The samples were denatured at 82° C. for 5 min. and hybridized overnight (20 hours). The stringency wash for compositions I and II was performed at 45° C. for 15 min. followed by a wash in 2×SCC at 45° C. for 3×5 min. The stringency wash for composition III was performed at 65° C. for 10 min. followed by a wash for 2×3 min. in Wash buffer (Vial 3, K5599).
Results:

| Stringency Wash | Temperature | Background | Signal Intensity | |
| --- | --- | --- | --- | --- |
| | | | DNA | PNA |
| SL (I) | 45° C./15 min | +0 | 1½-2 | 2½ |
| GBL (II) | 45° C./15 min | +0-½ | 2½-3 | 2½ |
| Reference (III) | 65° C./10 min | +0-½ | 2-2½ | 2½ |

These results show that at 45° C., the buffers of the invention produce similar levels of background as traditional stringent wash buffers at 65° C. Thus, the buffers of the invention can be used to produce low background under low temperature stringency wash conditions.

Example 26

This example compares the background and signal intensity as a function of the stringency wash conditions.

This example used a standard sales vial of HER2PharmDx probe mix (K5331, Dako) containing 10 ng/μL HER2 TxRed labeled DNA probe and (600 nM) of CEN17 PNA probes, 45% formamide, 10% dextran sulfate, 300 mM NaCl, 5 mM Phosphate buffer, 5 μM unlabelled blocking PNAs.

Stringency wash composition I: 0.1×SSC (pH 7.0), 20% EC

Stringency wash composition II, 0.5×SSC (pH 7.0), 20% EC

Stringency wash composition III: 1×SSC (pH 7.0), 20% EC

Stringency wash composition IV: 1× Stringency Buffer vial 4, K5599 (Dako)

The samples were denatured at 82° C. for 5 min. and hybridized overnight (20 hours). The stringency wash for compositions I-III was performed at 45° C. for 15 min followed by a wash in 2×SCC at 45° C. for 3×5 min, then washed 1×3 min. in Wash buffer (Vial 3, K5599). The stringency wash for composition IV was performed at 65° C. for 10 min. followed by a wash for 2×3 min. in Wash buffer (Vial 3, K5599).

Results:

| Stringency Wash | Temperature | Background | Signal Intensity DNA | PNA |
|---|---|---|---|---|
| 0.1×SSC (I) | 45° C./15 min | +1 | 2½-3 | 2½-3 |
| 0.5×SSC (II) | 45° C./15 min | +1 | 2-3 | 2½-3 |
| 1×SSC (III) | 45° C./15 min | +0-2 | 2½-3 | 2½-3 |
| Reference (IV) | 65° C./10 min | +1 | 2½-3 | 2½ |

These results show that at 45° C., the buffers of the invention produce similar levels of background as traditional stringent wash buffers at 65° C. Thus, the buffers of the invention can be used to produce low background under low temperature stringency wash conditions with different salt concentrations.

FURTHER EMBODIMENTS

Embodiment 1

A kit for performing a hybridization application comprising:
at least one nucleic acid sequence; and
an aqueous composition for performing a stringent wash, said composition comprising at least one polar aprotic solvent in an amount effective to denature non-complementary sequences in a hybridization product, and a hybridization solution,
wherein the polar aprotic solvent is not dimethyl sulfoxide (DMSO).

Embodiment 2

The kit according to embodiment 1, wherein the concentration of polar aprotic solvent in the aqueous composition is about 1% to 95% (v/v)

Embodiment 3

The kit according to embodiment 1 or 2, wherein the concentration of polar aprotic solvent in the aqueous composition is 5% to 10% (v/v).

Embodiment 4

The kit according to embodiment 1 or 2, wherein the concentration of polar aprotic solvent in the aqueous composition is 10% to 20% (v/v).

Embodiment 5

The kit according to embodiment 1 or 2, wherein the concentration of polar aprotic solvent in the aqueous composition is 30% to 95% (v/v).

Embodiment 6

The kit according to any one of embodiments 1 to 5, wherein the aqueous composition is non-toxic.

Embodiment 7

The kit according to any one of embodiments 1 to 6, with the proviso that the aqueous composition does not contain formamide.

Embodiment 8

The kit according to embodiment 6, with the proviso that the aqueous composition contains less than 25% formamide.

Embodiment 9

The kit according to embodiment 8, with the proviso that the aqueous composition contains less than 10% formamide.

Embodiment 10

The kit according to embodiment 9, with the proviso that the aqueous composition contains less than 2% formamide.

Embodiment 11

The kit according to embodiment 10, with the proviso that the aqueous composition contains less than 1% formamide.

Embodiment 12

The kit according to any of embodiments 1 to 11, wherein the polar aprotic solvent has lactone, sulfone, nitrile, sulfite, and/or carbonate functionality.

Embodiment 13

The kit according to any one of embodiments 1 to 12, wherein the polar aprotic solvent has a dispersion solubility parameter between 17.7 to 22.0 $MPa^{1/2}$, a polar solubility parameter between 13 to 23 $MPa^{1/2}$, and a hydrogen bonding solubility parameter between 3 to 13 $MPa^{1/2}$.

Embodiment 14

The kit according to any one of embodiments 1 to 13, wherein the polar aprotic solvent has a cyclic base structure.

Embodiment 15

The kit according to any one of embodiments 1 to 13, wherein the polar aprotic solvent is selected from the group consisting of:

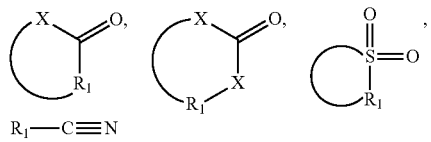

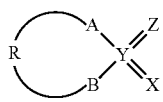

where X is O and R1 is alkyldiyl, and

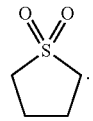

where X is optional and if present, is chosen from O or S, where Z is optional and if present, is chosen from O or S, where A and B independently are O or N or S or part of the alkyldiyl or a primary amine, where R is alkyldiyl, and where Y is O or S or C.

Embodiment 16

The kit according to any one of embodiments 1 to 15, wherein the polar aprotic solvent is selected from the group consisting of: acetanilide, acetonitrile, N-acetyl pyrrolidone, 4-amino pyridine, benzamide, benzimidazole, 1,2,3-benzotriazole, butadienedioxide, 2,3-butylene carbonate, γ-butyrolactone, caprolactone (epsilon), chloro maleic anhydride, 2-chlorocyclohexanone, chloroethylene carbonate, chloronitromethane, citraconic anhydride, crotonlactone, 5-cyano-2-thiouracil, cyclopropylnitrile, dimethyl sulfate, dimethyl sulfone, 1,3-dimethyl-5-tetrazole, 1,5-dimethyl tetrazole, 1,2-dinitrobenzene, 2,4-dinitrotoluene, dipheynyl sulfone, 1,2-dinitrobenzene, 2,4-dinitrotoluene, dipheynyl sulfone, epsilon-caprolactam, ethanesulfonylchloride, ethyl ethyl phosphinate, N-ethyl tetrazole, ethylene carbonate, ethylene trithiocarbonate, ethylene glycol sulfate, glycol sulfite, furfural, 2-furonitrile, 2-imidazole, isatin, isoxazole, malononitrile, 4-methoxy benzonitrile, 1-methoxy-2-nitrobenzene, methyl alpha bromo tetronate, 1-methyl imidazole, N-methyl imidazole, 3-methyl isoxazole, N-methyl morpholine-N-oxide, methyl phenyl sulfone, N-methylpyrrolidinone, methyl sulfolane, methyl-4-toluenesulfonate, 3-nitroaniline, nitrobenzimidazole, 2-nitrofuran, 1-nitroso-2-pyrrolidinone, 2-nitrothiophene, 2-oxazolidinone, 9,10-phenanthrenequinone, N-phenyl sydnone, phthalic anhydride, picolinonitrile (2-cyanopyridine), 1,3-propane sultone, β-propiolactone, propylene carbonate, 4H-pyran-4-thione, 4H-pyran-4-one (γ-pyrone), pyridazine, 2-pyrrolidone, saccharin, succinonitrile, sulfanilamide, sulfolane, 2,2,6,6-tetrachlorocyclohexanone, tetrahydrothiapyran oxide, tetramethylene sulfone (sulfolane), thiazole, 2-thiouracil, 3,3,3-trichloro propene, 1,1,2-trichloro propene, 1,2,3-trichloro propene, trimethylene sulfide-dioxide, and trimethylene sulfite.

Embodiment 17

The kit according to any one of embodiments 1 to 15, wherein the polar aprotic solvent is selected from the group consisting of:

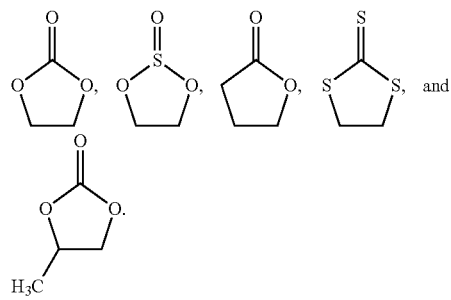

Embodiment 18

The kit according to any one of embodiments 1 to 15, wherein the polar aprotic solvent is:

Embodiment 19

The kit according to any one of embodiments 1 to 18, wherein the aqueous composition further comprises at least one additional component selected from the group consisting of: buffering agents, salts, accelerating agents, chelating agents, and detergents.

Embodiment 20

The kit according to embodiment 19, wherein the salts are NaCl and/or phosphate buffer and/or citrate buffer.

Embodiment 21

The kit according to embodiment 19, wherein the salts are NaCl and/or phosphate buffer and/or SSC.

Embodiment 22

The kit according to embodiment 20, wherein the NaCl is present at a concentration of 0 mM to 1200 mM and/or the citrate buffer is present at a concentration of 0 mM to 100 mM.

Embodiment 23

The kit according to embodiment 22, wherein the NaCl is present at a concentration of 50 mM to 600 mM and/or the citrate buffer is present at a concentration of 5 mM to 50 mM.

Embodiment 24

The kit according to embodiment 19, wherein the accelerating agent is selected from the group consisting of: formamide, DMSO, glycerol, propylene glycol, 1,2-propanediol, diethylene glycol, ethylene glycol, glycol, 1,2 propanediol, and 1,3 propanediol.

Embodiment 25

The kit according to embodiment 24, wherein the formamide is present at a concentration of 0.1-5%, the DMSO is present at a concentration of 0.01% to 10%, the glycerol, propylene glycol, 1,2-propanediol, diethylene glycol, ethylene glycol, glycol, 1,2 propanediol, and 1,3 propanediol are present at a concentration of 0.1% to 10%, and the citric acid buffer is present at a concentration of 1 mM to 100 mM.

Embodiment 26

The kit according to any one of embodiments 1-25, wherein the aqueous composition comprises 50% of at least one polar aprotic solvent and 0.05× to 4×SSC.

Embodiment 27

The kit according to any one of embodiments 1-25, wherein the aqueous composition comprises 20% of at least one polar aprotic solvent and 2×SSC.

Embodiment 28

The kit according to any one of embodiments 1-25, wherein the aqueous composition comprises 15% of at least one polar aprotic solvent and 2×SSC.

Embodiment 29

The kit according to any one of embodiments 1-28, wherein the aqueous composition comprises more than one phase at room temperature.

Embodiment 30

The kit according to embodiment 29, wherein the aqueous composition comprises two phases at room temperature.

Embodiment 31

The kit according to embodiment 29, wherein the aqueous composition comprises three phases at room temperature.

Embodiment 32

A method for performing a stringent wash step in a hybridization application comprising:
a. providing a hybridization product comprising a first nucleic acid sequence hybridized to a second nucleic acid sequence,
b. providing an aqueous composition comprising at least one polar aprotic solvent in an amount effective to denature non-complementary double-stranded nucleotide sequences, and
c. combining the hybridization product and the aqueous composition for at least a time period sufficient to denature any non-complementary binding between the first and second nucleic acid sequences.
wherein the polar aprotic solvent is not dimethyl sulfoxide (DMSO).

Embodiment 33

A method for performing a stringent wash step in a hybridization application comprising:
a. providing a hybridization product comprising a first nucleic acid sequence hybridized to a second nucleic acid sequence,
b. providing an aqueous composition as defined in any of embodiments 1 to 31, and
c. combining the hybridization product and the aqueous composition for at least a time period sufficient to denature any non-complementary binding between the first and second nucleic acid sequences.

Embodiment 34

The method according to embodiment 32, wherein the polar aprotic solvent is defined according to any of embodiments 2-5 or 12-18.

Embodiment 35

The method according to embodiment 32 or 33, wherein a sufficient amount of energy to denature any non-complementary binding between the first and second nucleic acid sequences is provided.

Embodiment 36

The method according to embodiment 35, wherein the energy is provided by heating the combination produced in (c).

Embodiment 37

The method according to embodiment 36, wherein the energy is provided by the use of microwaves, hot baths, hot plates, heat wire, peltier element, induction heating, or heat lamps.

Embodiment 38

The method according to embodiment 36, wherein the combination produced in (c) is heated to less than 70° C., such as, for example, 65° C., 62° C., 60° C., 55° C., 52° C., 50° C., 45° C., 42° C., 40° C., 35° C., 30° C., or room temperature.

Embodiment 39

The method according to any of embodiments 32 to 38, wherein the denaturation of any non-complementary binding between the first and second nucleic acid sequences occurs in less than 1 hour, such as, for example, 45 minutes, 30 minutes, 15 minutes, 10 minutes, 5 minutes, or 1 minute.

Embodiment 40

The method according to any one of embodiments 32-39, wherein the first nucleic acid sequence is in a biological sample.

Embodiment 41

The method according to embodiment 40, wherein the biological sample is a cytology or histology sample.

Embodiment 43

The method according to any one of embodiments 32-41, wherein the aqueous composition comprises one phase at room temperature.

Embodiment 44

The method according to any one of embodiments 32-43, wherein the aqueous composition comprises multiple phases at room temperature.

Embodiment 45

The method according to embodiment 44, wherein the aqueous composition comprises two phases at room temperature.

Embodiment 46

The method according to embodiment 44 or 45, wherein the phases of the aqueous composition are mixed.

Embodiment 47

An aqueous composition for performing a stringent wash in a hybridization application, said composition comprising at least one polar aprotic solvent in an amount effective to denature non-complementary sequences in a hybridization product, and a hybridization solution, wherein the polar aprotic solvent is not dimethyl sulfoxide (DMSO).

Embodiment 48

The aqueous composition of embodiment 47, wherein the concentration of polar aprotic solvent is defined as in any one of embodiments 2 to 5.

Embodiment 49

The aqueous composition of embodiment 47 or 48, wherein the polar aprotic solvent is defined as in any one of embodiments 12 to 18.

Embodiment 50

The aqueous composition of any one of embodiments 47 to 49, wherein the aqueous composition is further defined as in any one of embodiments 6 to 11 or 19 to 31.

Embodiment 51

Use of an aqueous composition comprising between 1 and 95% (v/v) of at least one polar aprotic solvent for a stringent wash step in a hybridization application.

Embodiment 52

Use of a composition according to embodiment 51, wherein the aqueous composition is defined as in any one of embodiments 1 to 31.

The invention claimed is:

1. A method for performing a stringent wash step in a hybridization application comprising:
    a) providing a hybridization product comprising a first nucleic acid sequence hybridized to a second nucleic acid sequence within a cell having a sample morphology,
    b) providing an aqueous composition for performing a stringent wash, said composition comprising at least one polar aprotic solvent in an amount effective to denature non-complementary sequences in a hybridization product, a hybridization solution, and 5%-40% dextran sulfate, wherein the polar aprotic solvent is not dimethyl sulfoxide (DMSO) and has lactone, sulfone, sulfite, or carbonate functionality, and
    c) combining the hybridization product and the aqueous composition at a temperature of 82° C. or less for at least a time period sufficient to denature any non-complementary binding between the first and second nucleic acid sequences within the cell such that the sample morphology is preserved.

2. The method according to claim 1, wherein a sufficient amount of energy to denature any non-complementary binding between the first and second nucleic acid sequences within the cell is provided.

3. The method according to claim 2, wherein the energy is provided by heating the combination produced in (c).

4. The method according to claim 3, wherein the combination produced in (c) is heated to less than 70° C.

5. The method according to claim 1, wherein the denaturation of any non-complementary binding between the first and second nucleic acid sequences within the cell occurs in less than 1 hour.

6. The method according to claim 1, wherein the first nucleic acid sequence is in a biological sample.

7. The method according to claim 6, wherein the biological sample is a cytology or histology sample.

8. The method according to claim 1, wherein the aqueous composition comprises one phase at room temperature.

9. The method according to claim 1, wherein the aqueous composition comprises multiple phases at room temperature.

10. The method according to claim 9, wherein the aqueous composition comprises two phases at room temperature.

11. The method according to claim 9, wherein the phases of the aqueous composition are mixed.

12. The method according to claim 1, wherein the aqueous composition further comprises one or more salts.

13. The method according to claim 12, wherein the salts are selected from the group consisting of sodium chloride, sodium phosphate, and magnesium phosphate.

14. The method according to claim 13, the sodium chloride is present at a concentration of 1 mM to 1200 mM.

15. The method according to claim 13, the sodium phosphate is present at a concentration of 10 mM to 500 mM.

* * * * *